US010913776B2

(12) United States Patent
Gambotto et al.

(10) Patent No.: US 10,913,776 B2
(45) Date of Patent: Feb. 9, 2021

(54) ZIKA VIRUS VACCINES

(71) Applicant: University of Pittsburgh—Of the Commonwealth System of Higher Education, Pittsburgh, PA (US)

(72) Inventors: Andrea A. Gambotto, Pittsburgh, PA (US); Eun Kim, Allison Park, PA (US); Geza Erdos, Wexford, PA (US); Louis D. Falo, Jr., Wexford, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 16/337,363

(22) PCT Filed: Sep. 29, 2017

(86) PCT No.: PCT/US2017/054469
§ 371 (c)(1),
(2) Date: Mar. 27, 2019

(87) PCT Pub. No.: WO2018/064558
PCT Pub. Date: Apr. 5, 2018

(65) Prior Publication Data
US 2020/0031874 A1 Jan. 30, 2020

Related U.S. Application Data

(60) Provisional application No. 62/402,557, filed on Sep. 30, 2016, provisional application No. 62/460,503, filed on Feb. 17, 2017.

(51) Int. Cl.

| | |
|---|---|
| *C07K 14/00* | (2006.01) |
| *A61K 39/12* | (2006.01) |
| *C07K 14/005* | (2006.01) |
| *A61P 31/14* | (2006.01) |
| *A61K 9/00* | (2006.01) |
| *C12N 7/00* | (2006.01) |
| *A61K 39/00* | (2006.01) |

(52) U.S. Cl.
CPC .......... *C07K 14/005* (2013.01); *A61K 9/0021* (2013.01); *A61K 39/12* (2013.01); *A61P 31/14* (2018.01); *C12N 7/00* (2013.01); *A61K 2039/54* (2013.01); *C07K 2319/02* (2013.01); *C07K 2319/30* (2013.01); *C07K 2319/70* (2013.01); *C12N 2770/24022* (2013.01); *C12N 2770/24034* (2013.01)

(58) Field of Classification Search
CPC . A61K 2039/6031; A61K 39/12; A61P 31/14; C07K 14/005; C07K 2319/02; C07K 2319/30; C07K 2319/40; C07K 2319/70; C12N 2770/24022; C12N 2770/24034
See application file for complete search history.

(56) References Cited

U.S. PATENT DOCUMENTS

| | | | |
|---|---|---|---|
| 8,834,423 | B2 | 9/2014 | Falo et al. |
| 9,944,019 | B2 | 4/2018 | Falo et al. |
| 2012/0207687 | A1 | 8/2012 | Falo et al. |
| 2016/0136407 | A1 | 5/2016 | Falo et al. |
| 2016/0271381 | A1 | 9/2016 | Falo et al. |
| 2018/0304062 | A1 | 10/2018 | Falo et al. |
| 2019/0000966 | A1 | 1/2019 | Falo et al. |

OTHER PUBLICATIONS

Dai L et al. Cell Host & Microbe. published on May 11, 2016, vol. 19, Issue 5, pp. 696-704.*
Deng et al. PLoS One Published Jan. 11, 2011, vol. 6, Issue 1, pp. 1-80) for claim 25.*
Bediz et al., "Dissolvable microneedle arrays for intradermal delivery of biologics: Fabrication and application," *Pharmaceutical Research* 31(1): 117-135 (Jan. 1, 2014).
Dowd et al., "Rapid development of a DNA vaccine for Zika virus," *Science* 354(6309): 237-240 (Epub Sep. 22, 2016).
Du et al., "A recombinant vaccine of H5N1 HA1 fused with foldon and human IgG Fc induced complete cross-clade protection against divergent H5N1 viruses," *PLoS One* 6(1):e16555(9 pages) (Jan. 27, 2012).
International Search Report from parent PCT Application No. PCT/US2017/054469, 4 pages (dated Dec. 4, 2017).
Kim et al., "Preventative vaccines for Zika virus outbreak: Preliminary evaluation," *EBioMedicine* 13: 315-320 (Epub 2016 Oct. 3, 2016).
Kim et al., "Tribody: robust self-assembled trimeric targeting ligands with high stability and significantly improved target-binding strength," *Biochemistry* 52(41):7283-7294 (Epub Oct. 3, 2013).
Larocca et al., "Vaccine protection against Zika virus from Brazil," *Nature* 536(7617): 474-478 (Aug. 25, 2016).
Written Opinion from parent PCT Application No. PCT/US2017/054469, 6 pages (dated Dec. 4, 2017).

* cited by examiner

*Primary Examiner* — Bao Q Li
(74) *Attorney, Agent, or Firm* — Klarquist Sparkman, LLP

(57) ABSTRACT

Disclosed is an immunogen comprising a fusion protein, wherein the fusion protein comprises a Zika virus (ZIKV) envelope protein, optionally a signal peptide, and a multimerization domain. The signal peptide is a premembrane (prM) signal peptide, an IgG signal peptide, or a human secretory signal peptide hidden Markov model, and the multimerization domain is an immunoglobulin Fc domain, a T4 fibritin foldon trimerization domain, or a human collagen XV trimerization domain. Nucleic acids, vectors, and microneedle arrays including these compositions are disclosed. Methods of producing an immune response to ZIKV are also disclosed.

72 Claims, 13 Drawing Sheets

Specification includes a Sequence Listing.

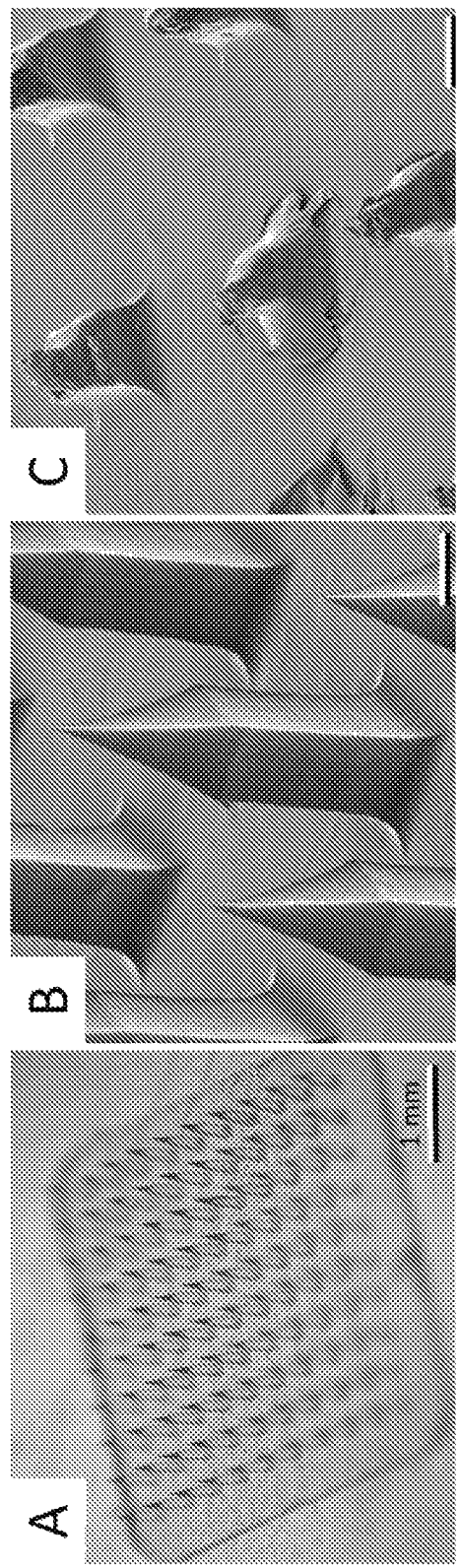

FIG. 8A    FIG. 8B    FIG. 8C
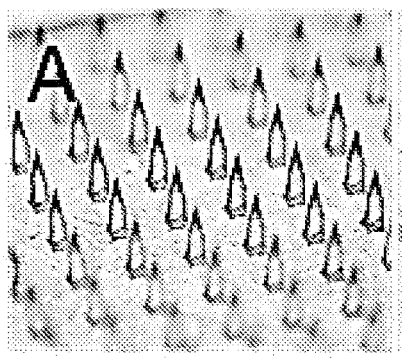 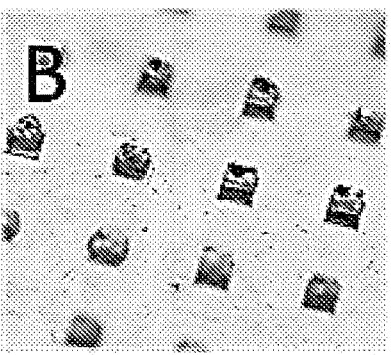 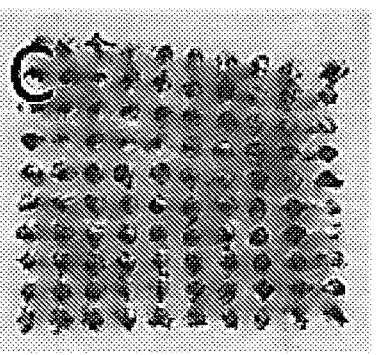
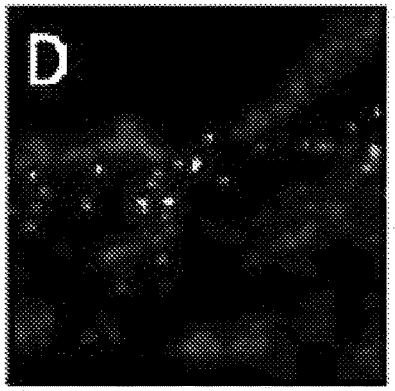 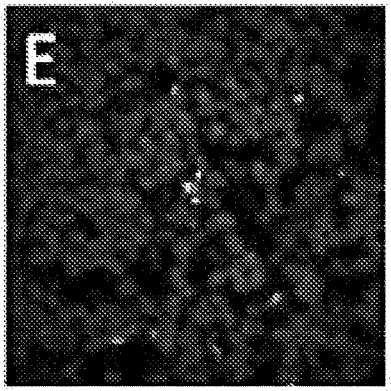 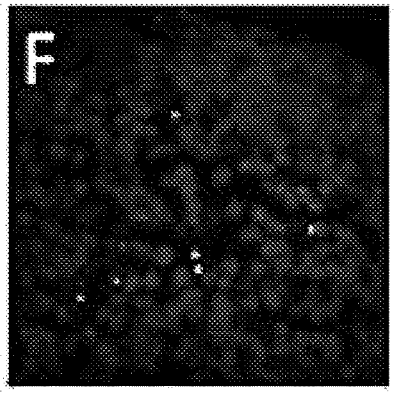
FIG. 8D    FIG. 8E    FIG. 8F

FIG. 9C

FIG. 11A
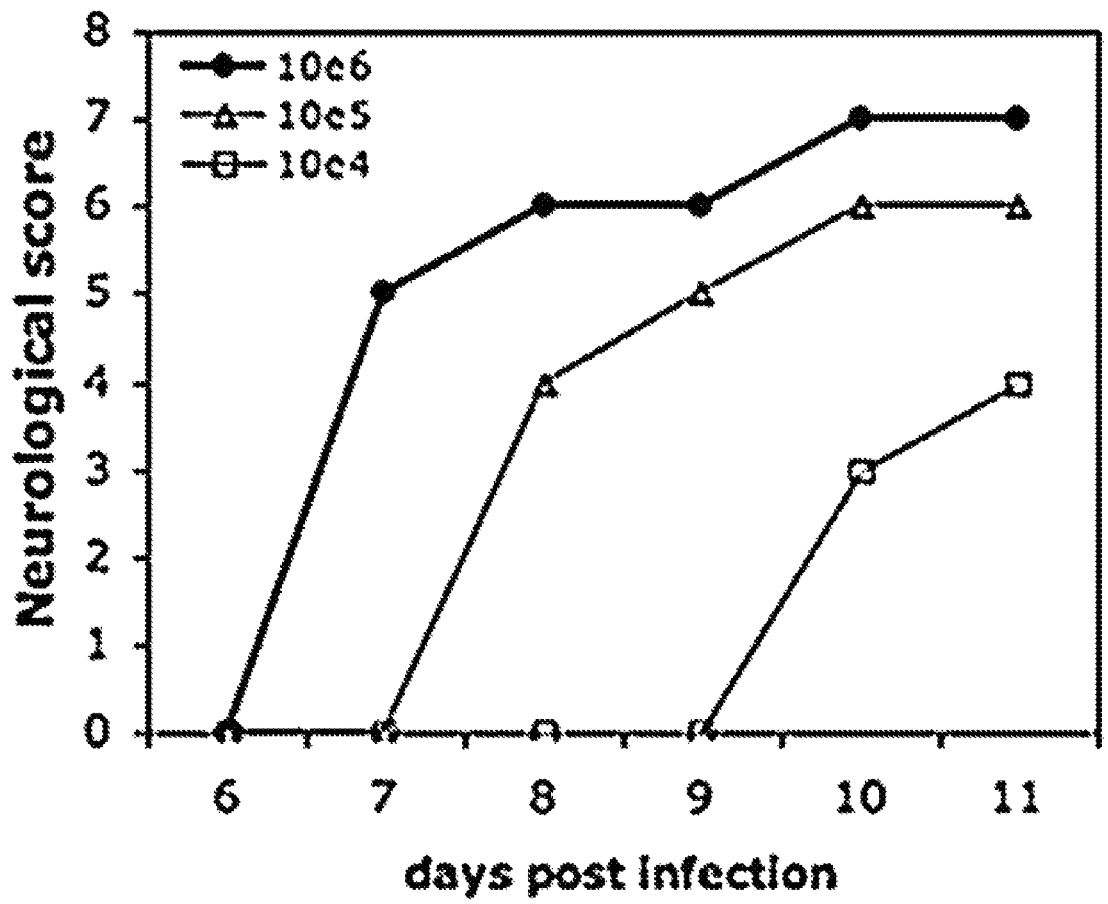
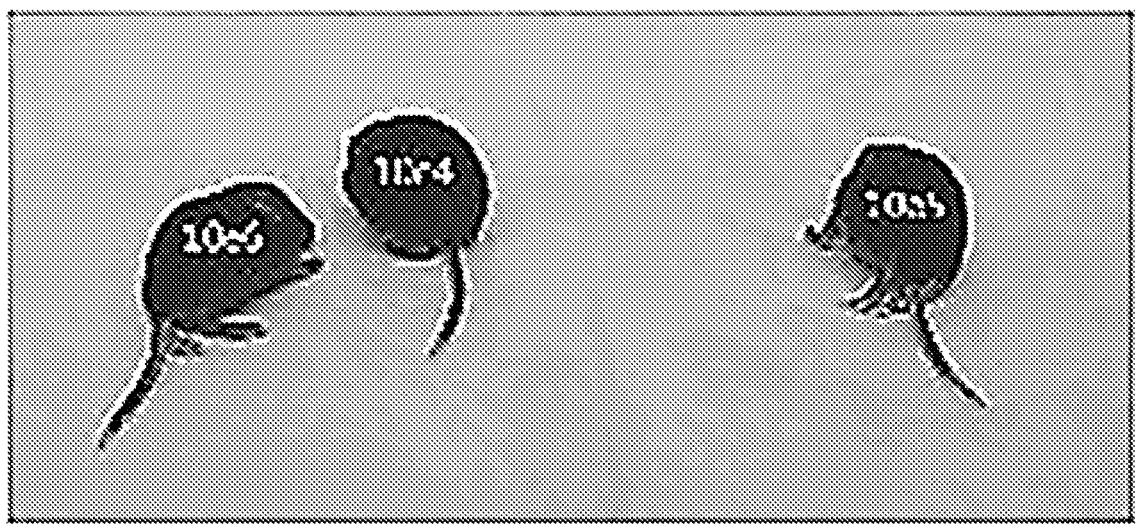
FIG. 11B

SEQUENCE LISTING

```
<160> NUMBER OF SEQ ID NOS: 13

<210> SEQ ID NO 1
<211> LENGTH: 4
<212> TYPE: PRT
<213> ORGANISM: Homo sapiens

<400> SEQUENCE: 1

Gln Val Gln Leu
1

<210> SEQ ID NO 2
<211> LENGTH: 21
<212> TYPE: PRT
<213> ORGANISM: Homo sapiens

<400> SEQUENCE: 2

Met Trp Trp Arg Leu Trp Trp Leu Leu Leu Leu Leu Leu Leu Leu Trp
1               5                   10                  15

Pro Met Val Trp Ala
            20

<210> SEQ ID NO 3
<211> LENGTH: 19
<212> TYPE: PRT
<213> ORGANISM: Mus musculus

<400> SEQUENCE: 3

Met Ala Val Leu Gly Leu Leu Phe Cys Leu Val Thr Phe Pro Ser Cys
1               5                   10                  15

Val Leu Ser

<210> SEQ ID NO 4
<211> LENGTH: 19
<212> TYPE: PRT
<213> ORGANISM: Homo sapiens

<400> SEQUENCE: 4

Met Glu Phe Gly Leu Ser Trp Val Phe Leu Val Ala Leu Phe Arg Gly
1               5                   10                  15

Val Gln Cys

<210> SEQ ID NO 5
<211> LENGTH: 22
<212> TYPE: PRT
<213> ORGANISM: Zika Virus

<400> SEQUENCE: 5
```

```
Arg Gly Ala Asp Thr Ser Val Gly Ile Val Gly Leu Leu Leu Thr Thr
1               5                   10                  15

Ala Met Ala Ala Glu Val
            20
```

```
<210> SEQ ID NO 6
<211> LENGTH: 405
<212> TYPE: PRT
<213> ORGANISM: Zika Virus

<400> SEQUENCE: 6
```

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
```

```
                    340                 345                 350
Thr Pro Val Gly Arg Leu Ile Thr Ala Asn

-continued

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
                435                 440                 445

Phe Gly Ala Ala Phe Lys Ser Leu
        450                 455

<210> SEQ ID NO 8
<211> LENGTH: 165
<212> TYPE: PRT
<213> ORGANISM: Homo sapiens

<400> SEQUENCE: 8

Thr Arg Arg Gly Ser Ala Tyr Tyr Met Tyr Leu Asp Arg Asn Asp Ala
1               5                   10                  15

Gly Glu Ala Ile Ser Phe Pro Thr Thr Leu Gly Met Asn Lys Cys Tyr
                20                  25                  30

Ile Gln Ile Met Asp Leu Gly His Met Cys Asp Ala Thr Met Ser Tyr
            35                  40                  45

Glu Cys Pro Met Leu Asp Glu Gly Val Glu Pro Asp Asp Val Asp Cys
50                  55                  60

Trp Cys Asn Thr Thr Ser Thr Trp Val Val Tyr Gly Thr Cys His His
65                  70                  75                  80

Lys Lys Gly Glu Ala Arg Arg Ser Arg Arg Ala Val Thr Leu Pro Ser
                85                  90                  95

His Ser Thr Arg Lys Leu Gln Thr Arg Ser Gln Thr Trp Leu Glu Ser
            100                 105                 110

Arg Glu Tyr Thr Lys His Leu Ile Arg Val Glu Asn Trp Ile Phe Arg
        115                 120                 125

Asn Pro Gly Phe Ala Leu Ala Ala Ala Ile Ala Trp Leu Leu Gly
    130                 135                 140

Ser Ser Thr Ser Gln Lys Val Ile Tyr Leu Val Met Ile Leu Leu Ile
145                 150                 155                 160

Ala Pro Ala Tyr Ser
                165

<210> SEQ ID NO 9
<211> LENGTH: 229
<212> TYPE: PRT
<213> ORGANISM: Homo sapiens

<400> SEQUENCE: 9

```
Asp Lys Thr His Thr Cys Pro Ser Arg Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Leu His Glu Ala Leu His Ser His Tyr Thr Gln Lys Ser Leu Ser
210                 215                 220

Leu Ser Pro Gly Lys
225

<210> SEQ ID NO 10
<211> LENGTH: 27
<212> TYPE: PRT
<213> ORGANISM: Bacteriophage T4

<400> SEQUENCE: 10

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 11
<211> LENGTH: 63
<212> TYPE: PRT
<213> ORGANISM: Homo sapiens

<400> SEQUENCE: 11

Val Thr Ala Phe Ser Asn Met Asp Asp Met Leu Gln Lys Ala His Leu
1               5                   10                  15

Val Ile Glu Gly Thr Phe Ile Tyr Leu Arg Asp Ser Thr Glu Phe Phe
            20                  25                  30

Ile Arg Val Arg Asp Gly Trp Lys Lys Leu Gln Leu Gly Glu Leu Ile
        35                  40                  45

Pro Ile Pro Ala Asp Ser Pro Pro Pro Ala Leu Ser Ser Asn
    50                  55                  60
```

<210> SEQ ID NO 12
<211> LENGTH: 822
<212> TYPE: PRT
<213> ORGANISM: Artificial Sequence
<220> FEATURE:
<223> OTHER INFORMATION: Immunogen

<400> SEQUENCE: 12

```
Met Ala Val Leu Gly Leu Leu Phe Cys Leu Val Thr Phe Pro Ser Cys
1               5                   10                  15

Val Leu Ser Gln Val Gln Leu Thr Arg Arg Gly Ser Ala Tyr Tyr Met
            20                  25                  30

Tyr Leu Asp Arg Asn Asp Ala Gly Glu Ala Ile Ser Phe Pro Thr Thr
        35                  40                  45

Leu Gly Met Asn Lys Cys Tyr Ile Gln Ile Met Asp Leu Gly His Met
    50                  55                  60

Cys Asp Ala Thr Met Ser Tyr Glu Cys Pro Met Leu Asp Glu Gly Val
65                  70                  75                  80

Glu Pro Asp Asp Val Asp Cys Trp Cys Asn Thr Thr Ser Thr Trp Val
                85                  90                  95

Val Tyr Gly Thr Cys His His Lys Lys Gly Glu Ala Arg Arg Ser Arg
            100                 105                 110

Arg Ala Val Thr Leu Pro Ser His Ser Thr Arg Lys Leu Gln Thr Arg
        115                 120                 125

Ser Gln Thr Trp Leu Glu Ser Arg Glu Tyr Thr Lys His Leu Ile Arg
    130                 135                 140

Val Glu Asn Trp Ile Phe Arg Asn Pro Gly Phe Ala Leu Ala Ala Ala
145                 150                 155                 160

Ala Ile Ala Trp Leu Leu Gly Ser Ser Thr Ser Gln Lys Val Ile Tyr
                165                 170                 175

Leu Val Met Ile Leu Leu Ile Ala Pro Ala Tyr Ser Ile Arg Cys Ile
            180                 185                 190

Gly Val Ser Asn Arg Asp Phe Val Glu Gly Met Ser Gly Gly Thr Trp
        195                 200                 205

Val Asp Val Val Leu Glu His Gly Gly Cys Val Thr Val Met Ala Gln
    210                 215                 220

Asp Lys Pro Thr Val Asp Ile Glu Leu Val Thr Thr Thr Val Ser Asn
225                 230                 235                 240

Met Ala Glu Val Arg Ser Tyr Cys Tyr Glu Ala Ser Ile Ser Asp Met
                245                 250                 255

Ala Ser Asp Ser Arg Cys Pro Thr Gln Gly Glu Ala Tyr Leu Asp Lys
            260                 265                 270

Gln Ser Asp Thr Gln Tyr Val Cys Lys Arg Thr Leu Val Asp Arg Gly
        275                 280                 285

Trp Gly Asn Gly Cys Gly Leu Phe Gly Lys Gly Ser Leu Val Thr Cys
    290                 295                 300

Ala Lys Phe Ala Cys Ser Lys Lys Met Thr Gly Lys Ser Ile Gln Pro
305                 310                 315                 320

Glu Asn Leu Glu Tyr Arg Ile Met Leu Ser Val His Gly Ser Gln His
                325                 330                 335

Ser Gly Met Ile Val Asn Asp Thr Gly His Glu Thr Asp Glu Asn Arg
            340                 345                 350

Ala Lys Val Glu Ile Thr Pro Asn Ser Pro Arg Ala Glu Ala Thr Leu
        355                 360                 365
```

-continued

```
Gly Gly Phe Gly Ser Leu Gly Leu Asp Cys Glu Pro Arg Thr Gly Leu
        370                 375                 380
Asp Phe Ser Asp Leu Tyr Tyr Leu Thr Met Asn Asn Lys His Trp Leu
385                 390                 395                 400
Val His Lys Glu Trp Phe His Asp Ile Pro Leu Pro Trp His Ala Gly
                405                 410                 415
Ala Asp Thr Gly Thr Pro His Trp Asn Asn Lys Glu Ala Leu Val Glu
            420                 425                 430
Phe Lys Asp Ala His Ala Lys Arg Gln Thr Val Val Leu Gly Ser
            435                 440                 445
Gln Glu Gly Ala Val His Thr Ala Leu Ala Gly Ala Leu Glu Ala Glu
    450                 455                 460
Met Asp Gly Ala Lys Gly Arg Leu Ser Ser Gly His Leu Lys Cys Arg
465                 470                 475                 480
Leu Lys Met Asp Lys Leu Arg Leu Lys Gly Val Ser Tyr Ser Leu Cys
                485                 490                 495
Thr Ala Ala Phe Thr Phe Thr Lys Ile Pro Ala Glu Thr Leu His Gly
                500                 505                 510
Thr Val Thr Val Glu Val Gln Tyr Ala Gly Thr Asp Gly Pro Cys Lys
            515                 520                 525
Val Pro Ala Gln Met Ala Val Asp Met Gln Thr Leu Thr Pro Val Gly
        530                 535                 540
Arg Leu Ile Thr Ala Asn Pro Val Ile Thr Glu Ser Thr Glu Asn Ser
545                 550                 555                 560
Lys Met Met Leu Glu Leu Asp Pro Pro Phe Gly Asp Ser Tyr Ile Val
                565                 570                 575
Ile Gly Val Gly Glu Lys Lys Ile Thr His His Trp His Arg Ser Gly
                580                 585                 590
Ser Asp Lys Thr His Thr Cys Pro Ser Arg Pro Cys Pro Ala Pro Glu
            595                 600                 605
Leu Leu Gly Gly Pro Ser Val Phe Leu Phe Pro Lys Pro Lys Asp
        610                 615                 620
Thr Leu Met Ile Ser Arg Thr Pro Glu Val Thr Cys Val Val Val Asp
625                 630                 635                 640
Val Ser His Glu Asp Pro Glu Val Lys Phe Asn Trp Tyr Val Asp Gly
                645                 650                 655
Val Glu Val His Asn Ala Lys Thr Lys Pro Arg Glu Glu Gln Tyr Asn
                660                 665                 670
Ser Thr Tyr Arg Val Val Ser Val Leu Thr Val Leu His Gln Asp Trp
            675                 680                 685
Leu Asn Gly Lys Glu Tyr Lys Cys Lys Val Ser Asn Lys Ala Leu Pro
    690                 695                 700
Ala Pro Ile Glu Lys Thr Ile Ser Lys Ala Lys Gly Gln Pro Arg Glu
705                 710                 715                 720
Pro Gln Val Tyr Thr Leu Pro Pro Ser Arg Asp Glu Leu Thr Lys Asn
                725                 730                 735
Gln Val Ser Leu Thr Cys Leu Val Lys Gly Phe Tyr Pro Ser Asp Ile
            740                 745                 750
Ala Val Glu Trp Glu Ser Asn Gly Gln Pro Glu Asn Asn Tyr Lys Thr
                755                 760                 765
Thr Pro Pro Val Leu Asp Ser Asp Gly Ser Phe Phe Leu Tyr Ser Lys
770                 775                 780
Leu Thr Val Asp Lys Ser Arg Trp Gln Gln Gly Asn Val Phe Ser Cys
```

```
                785                 790                 795                 800
Ser Val Leu His Glu Ala Leu His Ser His Tyr Thr Gln Lys Ser Leu
                    805                 810                 815
Ser Leu Ser Pro Gly Lys
        820

<210> SEQ ID NO 13
<211> LENGTH: 4472
<212> TYPE: DNA
<213> ORGANISM: Artificial Sequence
<220> FEATURE:
<223> OTHER INFORMATION: Nucleic Acid Encoding Immunogen

<400> SEQUENCE: 13
aagcttgcca ccatggccac ctcagcaagt tcccacttga acaaaggcat caagcaaatg      60
tacatgtccc tgccccaggg tgagaaagtc aagccatgt atatctgggt tgatggtacc     120
ggagaaggac tgcgctgcaa aacccgcacc ctggactgtg agcccaagtg tgtagaagag     180
ttacctgagt ggaattttga tggctctagt acctttcagt ctgagagctc aacagtgac     240 atgtatctca gccctgttgc catgtttcgg gacccct tcc gcaaagagcc aacaagctg     300 gtgttctgtg aagtcttcaa gtacaaccag aagcctgcag agaccaattt aagacacacg     360
tgtaaacgga taatggacat ggtgagcaac cagcacccct ggtttggaat ggaacaggag     420
tatactctct gggaacagat ggg caccct tttggttggc cttccgatgg cttccctggg     480
ccccaaggtc tgtattactg tggtgtgggc gcagacaaag cctatcgcag ggatatcatg     540
gaggctcact accgtgcctg cttgtatgct ggggtcaaga ttacaggaac atatgctgag     600
gtcaagcatg cccagtggga attccaaata ggaccctgtg aaggaatccg catgggagat     660
catctctggg tggcccgttt catcttgcat cgagtatgta aagactttgg agtaatagca     720 accttt gact ccaagcccat tctgggaac tggaatggtg caggctgcca taccaacttt     780
agtaccaaga ccatgcggga ggagaatggt ctgaagcaca tcaaggaggc cattgagaaa     840
ctaagcaagc ggcaccggta ccatattcga gcctacgatc caaggggggg gctggacaat     900
gcccgtcgtc tgactgggtt ccacaaaacg tccaacatca cgacttttc agctggcgtc     960 gccgatcgca gtgccagcat ccgcattccc cggactgtcg gccaggagaa gaaaggttac    1020
tttgaagccc gctgccccctc tgccaattgt gacccctttg cagtgacaga agccatcgtc    1080
cgcacatgcc ttctcaatga gactggcgac cagccctt cc aatacaaaaa cggcagcggc    1140
gcgaccaact ttagcctcct caagcaggcg ggggatgtgg aggagaaccc aggtcctatg    1200
gtgagcaagg gcgaggagct gttcaccggg gtggtgccca tcctggtcga gctggacggc    1260
gacgtaaacg gccacaagtt cagcgtgtcc ggcgagggcg agggcgatgc cacctacggc    1320
aagctgaccc tgaagttcat ctgcaccacc ggcaagctgc ccgtgccctg gcccaccctc    1380
gtgaccaccc tgacctacgg cgtgcagtgc ttcagccgct accccgacca catgaagcag    1440
cacgacttct tcaagtccgc catgcccgaa ggctacgtcc aggagcgcac catcttcttc    1500
aaggacgacg gcaactacaa gacccgcgcc gaggtgaagt tcgagggcga caccctggtg    1560
aaccgcatcg agctgaaggg catcgacttc aaggaggacg gcaacatcct ggggcacaag    1620
ctggagtaca actacaacag ccacaacgtc tatatcatgg ccgacaagca gaagaacggc    1680
atcaaggtga acttcaagat ccgccacaac atcgaggacg gcagcgtgca gctcgccgac    1740
cactaccagc agaacacccc catcggcgac ggccccgtgc tgctgcccga caaccactac    1800
ctgagcaccc agtccgccct gagcaaagac cccaacgaga agcgcgatca catggtcctg    1860
```

```
ctggagttcg tgaccgccgc cgggatcact ctcggcatgg acgagctgta caagggctcc     1920
ggccagtgta caaactacgc cctgcttaaa ttagccggcg acgtggagtc aaaccccggc     1980
cccgtcgaca tggccgttct gggtctcctg ttctgcctgg tcacattccc cagttgtgtg     2040
ctcagtcagg tgcagttgac taggcgggga agcgcctatt acatgtacct ggaccgaaac     2100
gatgccggcg aagccatctc cttccccacc acgctcggaa tgaacaaatg ctatatccag     2160
atcatggatc tagggcacat gtgcgacgcg accatgtcgt acgagtgtcc catgctggac     2220
gaaggcgttg agcctgacga cgtggactgc tggtgcaata ctactagcac ttgggtggtg     2280
tacgggacct gtcatcacaa gaagggcgag gcccggcgct cccgtcgcgc agtgaccctg     2340
ccctctcact caacccgcaa gctgcagact cggtcgcaga catggctgga gtcccgggag     2400
tacactaagc acctcattcg cgtggagaac tggatcttcc gcaaccccgg gtttgctctc     2460
gccgccgctg ccatcgcgtg gctgttagga agttccacgt cccagaaagt gatctacctg     2520
gttatgatcc tccttatcgc ccccgcctac tccatccgct gtattggggt gagtaaccgc     2580
gacttcgtgg aggggatgtc cggcggcacc tgggtggatg tggtgctgga gcacgggggc     2640
tgtgtgacgg tcatggcgca agacaagcct accgtggata tcgagctcgt gaccacaacc     2700
gtgtccaaca tggcagaggt ccggtcctat tgctatgaag ccagtatctc tgacatggcc     2760
agcgacagtc gctgcccgac gcaggggggag gcctatctcg acaagcagtc ggatacccaa     2820
tacgtgtgta gcggactct cgtggaccga ggctggggca acggctgcgg cctgttcgga     2880
aagggcagcc tcgtaacttg cgccaagttc gcgtgctcta agaagatgac cggtaagagt     2940
atccagccgg agaacctgga atacaggatc atgctctcgg tgcacggctc ccagcactcc     3000
ggcatgatcg ttaacgacac cggccacgaa accgatgaga accgcgctaa ggtggagatc     3060
accccaaact ccccccgggc ggaggctacc ctgggcgggt tcgggtcgct cgggctcgac     3120
tgtgagccca ggaccggcct ggatttctcg gatctgtact acctgaccat gaataataag     3180
cactggctgg tgcacaagga gtggttccac gacatcccgt taccctggca cgcaggcgcc     3240
gacaccggga cacctcactg gaacaacaag gaggccttag tcgagttcaa ggatgcccac     3300
gccaaacggc agaccgtggt ggtgttaggc tcccaggaag gggccgtgca caccgccctg     3360
gccggtgccc tggaggccga gatggatggc gccaaaggcc gcctgtcatc cggacacctg     3420
aagtgccgcc tcaagatgga caagttgagg ctgaaggggg tgtcttattc gctgtgtacc     3480
gcagccttca cgttcacaaa gatcccagcc gagacactgc acgggaccgt caccgtggag     3540
gttcagtacg ccgggaccga cggccgtgc aaggttcccg cccagatggc agtggacatg     3600
cagaccctga caccagtcgg ccgactcatt acggccaacc cagtcatcac cgagtccacg     3660
gagaactcca agatgatgct cgaactggac ccccctttcg tgacagttac atcgtgatc      3720 ggcgtgggcg aaaagaagat cactcaccac tggcatcggt caggatccga caagactcat     3780
acctgtccat cgcgcccttg ccccgccccc gagctccttg gcggtccatc cgtgttcctg     3840
tttccaccaa agccgaaaga taccctgatg atctcccgga cccccgaggt gacctgcgtg     3900
gtggtggacg tgagtcacga ggaccccgag gtgaagttca actggtacgt cgatggggtc     3960
gaggtgcaca acgcgaagac gaagccaagg gaggagcagt acaactccac ctacagggtg     4020
gtctcggttc tcaccgtcct gcaccaggac tggctgaatg gcaaggagta caagtgcaag     4080
gtgtcgaaca aggcactgcc cgcaccaatc gaaaagacaa tatccaaggc aaaaggacag     4140
ccgagagagc cccaggtgta taccctgccc ccgtcgcgag acgagctgac caagaatcag     4200
```

```
gtgagtctga cgtgcctggt gaagggcttt tatcccagcg acatcgctgt ggaatgggag    4260
agtaatggcc agcccgagaa caactataag accacccctc ccgtcctgga ttcggatggg    4320
agtttcttcc tgtactcgaa gctcactgtc gataagtccc ggtggcagca ggggaacgtg    4380
ttttcctgct ccgttctgca cgaagcgctg cattcgcact acacccagaa atcgcttagt    4440
ctctcccccg gcaagtaagc ggccgcctcg ag                                  4472
```

ZIKA VIRUS VACCINES

CROSS REFERENCE TO RELATED APPLICATION

This is a § 371 U.S. national stage of International Application No. PCT/US2017/054469, filed Sep. 29, 2017, which was published in English under PCT Article 21(2), and which claims the benefit of U.S. Provisional Application No. 62/402,557, filed on Sep. 30, 2016, and U.S. Provisional Application No. 62/460,503, filed on Feb. 17, 2017 which are herein incorporated by reference in their entirety.

FIELD

This relates to the field of vaccines, specifically to immunogens that can be used to induce an immune response to Zika virus.

BACKGROUND

Zika virus (ZIKV) is a mosquito-borne flavivirus of the Flaviviridae family that was first identified in Uganda in 1947. The virus has recently attracted global attention due to its rapid spread from Brazil to other countries in the Americas (Dick et al., 1952, Trans R Soc Trop Med Hyg, 46, 509-20; Zanluca et al., 2015, Mem Inst Oswaldo Cruz, 110, 569-72). The ZIKV outbreak in Brazil has been associated with a significant rise in the number of babies born with microcephaly (Zanluca et al., 2015, supra) and neurological disorders such as Guillain-Barré syndrome and has been declared a "Global Emergency" by the World Health Organization (WHO 2016 who.int/mediacentre/factsheets/zika/en/; WHO 2016 who.int/mediacentre/news/statements/2016/lst-emergency-committee-zika/en/; CDC 2016 cdc.gov/zika/). Concern over the spread of ZIKV to the Northern Hemisphere with its concomitant morbidity is spurring the search for an effective vaccine. ZIKV is related to dengue, yellow fever, Japanese encephalitis, and West Nile viruses (WNV), all of which are arthropod-borne flaviviruses. Like other flaviviruses, ZIKV contains a positive, single-stranded, genomic RNA encoding a polyprotein that is proteolytically processed to yield three structural proteins: the capsid (C), the precursor of membrane (prM), and the envelope (E), and seven nonstructural proteins (NS1, NS2a, NS2b, NS3, NS4a, NS4b, and NS5) (Dick et al., 1952, Trans R Soc Trop Med Hyg, 46, 509-20).

The successful development of flavivirus vaccines began 80 years ago in 1937 with the yellow fever YFV17D live-attenuated vaccine (Monath et al., 2008, N Engl J Med, 364, 1326-33). Since then, more than 600 million people have been vaccinated, with 98% protection and a >10 year persistence of vaccine-induced immunity (Barrett and Teuwen, 2009, Curr Opin Immunol, 21, 308-13). A need remains for vaccines for ZIKV.

SUMMARY

Disclosed is an immunogen comprising a fusion protein, wherein the fusion protein comprises a Zika virus (ZIKV) envelope protein, optionally a signal peptide, and a multimerization domain. The signal peptide is a premembrane (prM) signal peptide, an IgG signal peptide, or a human secretory signal peptide hidden Markov model, and the multimerization domain is an immunoglobulin Fc domain, a T4 fibritin foldon trimerization domain, or a human collagen XV trimerization domain. The fusion protein optionally can include a prM protein.

Nucleic acids and vectors encoding the immunogens and fusion proteins are also disclosed. In additional embodiments, disclosed are compositions including a therapeutically effective amount of the immunogen, fusion protein, nucleic acid molecule, and/or vector are provided. In addition microneedle arrays including these pharmaceutical compositions.

The use of these compositions and microneedle arrays to produce an immune response to ZIKV is also disclosed. These compositions and microneedle arrays can be used to treat or prevent an ZIKV infection in a subject, such as a human subject.

The foregoing and other objects, features, and advantages of the invention will become more apparent from the following detailed description, which proceeds with reference to the accompanying figures.

BRIEF DESCRIPTION OF THE DRAWINGS

(FIG. 2A) Experimental schedule representing the immunization timeline. C57BL/6 mice (n=5/group) were immunized subcutaneously with $1 \times 10^{11}$ viral particles of Ad.ZIKV-Efl or PBS as a negative control and boosted intranasally with the same amount of adenovirus two weeks later. MNA-ZIKV-rEfl was administered through intradermal delivery. (FIG. 2B) ZIKV-specific IgG antibody levels were measured at the indicated time points using ELISA. (FIG. 2C) The ZIKV-neutralizing titers at week 6 post-immunization were measured using Vero cells by determining the reciprocal of the highest serum dilution still giving a 50% reduction in plaque number by 50% (PRNT50), relative to samples incubated with pre-immunized control pooled sera. Statically significant differences (Tukey's test) are marked by bars and asterisks. *, $P<0.05$; ***, $P<0.001$. The same mean of neutralization was detected in two independent neutralizing tests with combined mouse sera.

(FIG. 6A) Schematic diagram shows a fusion protein of GS-EGFP-preMEFc linked 2A. (FIG. 2B) At 48 h post transfection, medium was collected, and cells were lysed. Expression in medium and cell lysate were measured by ELISA using goat anti-human IgG as a capture antibody and mouse anti-ZIKV as a detection antibody.

FIGS. 7A-7C. Microscopic images of an MNA. FIG. 7A) An MNA. FIG. 7B, 7C) Obelisk-shaped needles before (FIG. 7B) and after (FIG. 7C) application of the MNA to the skin. Notice the efficient degradation of the needles in (FIG. 7C). Scanning electron microscopy ×100.

FIGS. 8A-8F. Penetration and delivery of CMC microneedle cargo to mouse and human skin. Stereo micrographs of sharp pillar type patches before application to human skin (FIG. 8A) and after 5 min. Exposure (FIG. 8B) to freshly excised human skin explants where the tracer dye is deposited (FIG. 8C). Cross section of a mouse ear at the MNA insertion site demonstrating delivery of fluorescent tracer beads (FIG. 8D, DAPI and fluorescent particles). After 48 hours the fluorescent tracers were also detectable in the draining lymph nodes, where they were associated with macrophages (FIG. 8E, DAPI, F4/80 and fluorescent particles) and DCs (FIG. 8F, DAPI), CD11c and fluorescent particles). FIGS. 8A and 8B: 2.5× optical magnification, FIG. 8C: 1.6×, Panel D: 20×, FIGS. 8E and 8F: 60× optical magnification).

FIGS. 9A-9C. Recombinant Zika subunit vaccines. The expression plasmid encoding the codon-optimized Zika virus BeH815744 envelope preME gene as monomer, dimer or trimer, were generated as shown in the diagram.

FIGS. 11A-11B. ZIKV challenge mouse model. (FIG. 11A) Neurological score based on the severity of paralysis and loss of balance, (FIG. 11B) Hind limbs paralysis was observed on day 10 post infection in $10^6$ or $10^5$ pfu ZIKV infected mouse.

SEQUENCE LISTING

Figure 1:
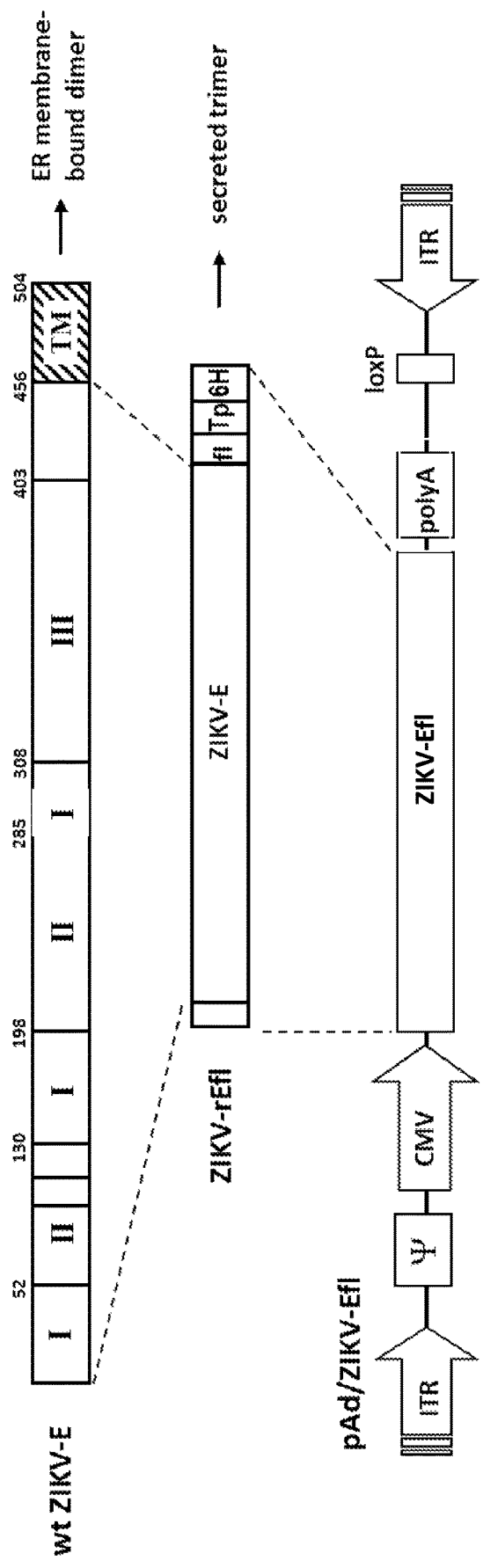
FIG. 1. Schematic representations of plasmid vector pAd/ZIKV-Efl. A shuttle vector carrying the gene encoding human secretory signal peptide hidden Markov model (SP-HMM), the extracellular portion of the ZIKV envelope gene (amino acids 216-794 of the polyprotein), BamH I-linked T4 fibritin foldon trimerization domain (fl), Tobacco Etch Virus Protease (Tp), and six histidine tag (6H) were designated as shown in the diagram. The three domains of ZIKV E are represented based on West Nile virus E: the positions of domain I, domain II, and domain III are shown (Mou et al., 2013, J Virol, 87, 9379-83). The vector was used to generate recombinant replication-deficient adenoviruses by homologous recombination with the adenoviral genomic DNA. Abbreviations are as follows: ITR, inverted terminal repeat; TM, transmembrane domain.

The nucleic and amino acid sequences listed are shown using standard letter abbreviations for nucleotide bases and for amino acids, as defined in 37 C.F.R. 1.822. Only one strand of each nucleic acid sequence is shown, but the complementary strand is understood as included by any reference to the displayed strand. The Sequence Listing is submitted as an ASCII text file Sequence_Listing, Feb. 12, 2019, size 25.8 KB], which is incorporated by reference herein. In the accompanying sequence listing:

SEQ ID NO: 1 is a linker sequence, and is present in human IgG.

SEQ ID NOs: 2-5 are signal peptides.

SEQ ID NOs: 6-7 are ZIKV envelope proteins

SEQ ID NO: 8 is a ZIKV prM protein.

SEQ ID NOs: 9-11 are multimerization domains.

SEQ ID NO: 12 is an exemplary immunogen.

SEQ ID NO: 13 is a nucleic acid sequence encoding an exemplary immunogen.

DETAILED DESCRIPTION

Immunogens are disclosed herein. These immunogens can be used to induce a neutralizing immune response, and were shown to protect against ZIKV challenge in an animal model of a ZIKV infection. The immunogens include a fusion protein, wherein the fusion protein comprises a Zika virus (ZIKV) envelope protein, optionally a signal peptide, and a multimerization domain. In some embodiments, the signal peptide can be a premembrane (prM) signal peptide, an IgG signal peptide, or a human secretory signal peptide hidden Markov model, and the multimerization domain can be an immunoglobulin Fc domain, a T4 fibritin foldon trimerization domain, or a human collagen XV trimerization domain. Any combination of these domains can be utilized.

In some embodiments, nucleic acids and vectors encoding these fusion proteins are provided. In some non-limiting examples, disclosed is a recombinant vector, such as an adenoviral vector, the expresses the disclosed immunogens.

The disclosed immunogens and viral vectors can be delivered to a subject to produce an immune response to ZIKV, such as a protective immune response. In some embodiments, delivery can be transcutaneously by microneedle arrays (MNAs), such as carboxymethyl cellulose (CMC) MNAs.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition, such as a vaccine) to a subject means to give, apply or bring the composition into contact with the subject. Administration can be accomplished by any of a number of routes, such as, for example, topical, oral, subcutaneous, intradermal intramuscular, intraperitoneal, intravenous, intrathecal and intramuscular.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen, such as a flavivirus E protein.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75% or at least about 90% relative to wild-type virus. Accordingly, an "attenuating mutation" is a mutation in the viral genome and/or an encoded polypeptide that results in an attenuated virus.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Capsid protein (C protein): A flavivirus structural protein that functions to package viral RNA into the nucleocapsid core during virus assembly. The C-terminal portion of the C protein includes an internal signal peptide (referred to herein as either C(ss) or prM signal peptide) for translocation of the prM protein into the endoplasmic reticulum, where cleavage of the C and prM proteins occurs. This signal peptide varies in length among different flaviviruses. For example, the C(ss) of both WNV and ZIKV is 18 amino acids, while the C(ss) of DEN viruses is 14 amino acids.

Codon-optimized: A "codon-optimized" nucleic acid refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

Conservative substitution: A substitution of one amino acid residue in a protein sequence for a different amino acid residue having similar biochemical properties. Typically, conservative substitutions have little to no impact on the activity of a resulting polypeptide. For example, ideally, a flavivirus protein (such as a prM, E, or non-structural protein) including one or more conservative substitutions (for example 1-10, 2-5, or 10-20, or no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected for additional testing by infecting cells with a virus containing a variant protein and determining its ability to replicate, by producing virus containing a variant protein and determining its neurovirulence or neuroinvasion properties, and/or by testing antibody cross-reactivity.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Control: A reference standard, for example a positive control or negative control. A positive control is known to provide a positive test result. A negative control is known to provide a negative test result. However, the reference standard can be a theoretical or computed result, for example a result obtained in a population.

Envelope glycoprotein (E protein): A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

Flavivirus non-structural protein: There are seven non-structural (NS) proteins of a flavivirus, NS1, NS2A, NS2B, NS3, NS4A, NS4B, and NS5, which are encoded by the portion of the flavivirus genome that is 3' to the structural proteins. NS1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222:159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). NS2 is cleaved into NS2A and NS2B. NS2A is involved in RNA replication and virus particle assembly and secretion and NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and RNA trafficking (Lindenbach and Rice, In: *Fields Virology*, Knipe and Howley, eds., Lippincott, Williams, and Wilkins, 991-1041, 2001). Finally, the NS5 protein is an RNA-dependent RNA polymerase involved in genome replication (Rice et al., *Science* 229:726-733, 1985). NS5 also shows methyltransferase activity commonly found in RNA capping enzymes (Koonin, *J. Gen. Virol.* 74:733-740, 1993).

Flavivirus structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, prM, and E)

are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope (Russell et al., *The Togaviruses: Biology, Structure, and Replication*, Schlesinger, ed., Academic Press, 1980). The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons. For example, a fusion protein includes an ZIKV protein fused to a heterologous protein.

Heterologous: Originating from a different genetic sources or species.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunize: To render a subject protected from an infectious disease, such as by vaccination.

Immunogen: A compound, composition, or substance which is capable, under appropriate conditions, of stimulating an immune response, such as the production of antibodies or a T-cell response in an animal, including compositions that are injected or absorbed into an animal. As used herein, an "immunogenic composition" is a composition comprising an immunogen (such as a Zika virus polypeptide).

Immunoglobulin Fc domain: The polypeptide including the constant region of an antibody excluding the first constant region immunoglobulin domain. Fc domain generally refers to the last two constant region immunoglobulin domains of IgA, IgD, and IgG, and the last three constant region immunoglobulin domains of IgE and IgM. An Fc domain may also include part or all of the flexible hinge N-terminal to these domains. For IgA and IgM, an Fc domain may or may not include the tailpiece, and may or may not be bound by the J chain. For IgG, the Fc domain includes immunoglobulin domains Cgamma2 and Cgamma3 (Cγ2 and Cγ3) and the lower part of the hinge between Cgamma1 (Cγ1) and Cγ2. Although the boundaries of the Fc domain may vary, the human IgG heavy chain Fc domain is usually defined to include residues C226 or P230 to its carboxyl-terminus, wherein the numbering is according to the EU index as in Kabat. For IgA, the Fc domain includes immunoglobulin domains Calpha2 and Calpha3 (Cα2 and Cα3) and the lower part of the hinge between Calpha1 (Cα1) and Cα2.

Isolated: An "isolated" or "purified" biological component (such as a nucleic acid, peptide, protein, protein complex, or particle) has been substantially separated, produced apart from, or purified away from other components in a preparation or other biological components in the cell of the organism in which the component occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Linker: A molecule or group of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker.

Multimerization Domain: A polypeptide sequence that functions to form multimers of an attached polypeptide, such as dimers, trimers, etc. under physiological conditions.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Operably linked: A first nucleic acid is operably linked to a second nucleic acid when the first nucleic acid is placed in a functional relationship with the second nucleic acid. Generally, operably linked DNA sequences are contiguous and, where necessary to join two protein coding regions, in the same reading frame. Operably linked nucleic acids include a first nucleic acid contiguous with the 5' or 3' end of a second nucleic acid. In other examples, a second nucleic acid is operably linked to a first nucleic acid when it is embedded within the first nucleic acid, for example, where the nucleic acid construct includes (in order) a portion of the first nucleic acid, the second nucleic acid, and the remainder of the first nucleic acid.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compositions, such as a chimeric virus, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Premembrane protein (prM protein): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Preventing, treating or ameliorating a disease: "Preventing" a disease refers to inhibiting the full development of a disease or infection, such as a ZIKV infection, from a subsequent exposure. "Treating" refers to a therapeutic intervention that ameliorates a sign or symptom of a disease or pathological condition after it has begun to develop. "Ameliorating" refers to the reduction in the number or severity of one or more signs or symptoms of a disease or infection. Prime-boost vaccination: An immunotherapy including administration of a first immunogenic composition (the primer vaccine) followed by administration of a second immunogenic composition (the booster vaccine) to a subject to elicit an immune response. The primer vaccine and/or the booster vaccine include a vector (such as a viral vector, RNA, or DNA vector) expressing the antigen to which the immune response is directed, or can include a protein immunogen. The booster vaccine is administered to the subject after the primer vaccine; the skilled artisan will understand a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Purified: The term purified does not require absolute purity; rather, it is intended as a relative term. Thus, for example, a purified nucleic acid preparation is one in which the nucleic acid is more enriched than the nucleic acid is in its natural environment (such as within a cell) or in a preparation or production vessel. In other examples, a purified virus preparation is one in which the virus is more enriched than in a cell or organism, a preparation, or a production vessel. A purified nucleic acid or virus also includes one that is substantially free of undesired components, such as an inactivating agent. Preferably, a preparation is purified such that the nucleic acid or virus represents at least 50% of the total content of the preparation. In some embodiments, a purified preparation contains at least 60%, at least 70%, at least 80%, at least 85%, at least 90%, at least 95%, at least 98%, at least 99%, or more of the nucleic acid or virus.

Recombinant nucleic acid: A nucleic acid molecule (or protein or virus) that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids and proteins that have been altered solely by addition, substitution, or deletion of a portion of a natural nucleic acid molecule or protein.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Homologs and variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 80% identity" (or similar language) refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence. As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-30 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region).

Subject: Living multi-cellular vertebrate organisms, a category that includes both human and non-human mammals (such as mice, rats, rabbits, sheep, horses, cows, and non-human primates).

Therapeutically effective amount: A quantity of a specified agent (such as a chimeric virus) sufficient to achieve a desired effect in a subject being treated with that agent. For example, this may be the amount of a virus vaccine useful for eliciting an immune response in a subject and/or for preventing infection by the virus. In the context of the present disclosure, a therapeutically effective amount of a Zika virus vaccine, for example, is an amount sufficient to increase resistance to, prevent, ameliorate, and/or treat infection caused by Zika virus in a subject without causing a substantial cytotoxic effect in the subject. The effective amount of a Zika virus vaccine (or Zika virus immunogenic composition) useful for increasing resistance to, preventing, ameliorating, and/or treating infection in a subject will be dependent on, for example, the subject being treated, the manner of administration of the therapeutic composition and other factors.

Transformed: A "transformed" cell is a cell into which has been introduced a nucleic acid molecule (such as a heterologous nucleic acid) by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, inhibition, amelioration, or treatment of infectious, such as ZIKV infections, or other types of disease. The immunogenic material may include attenuated or inactivated (killed) microorganisms (such as bacteria or viruses), or antigenic proteins, peptides or DNA derived from them. An attenuated virus is a virulent organism that has been modified to produce a less virulent form, but nevertheless retains the ability to elicit antibodies and cell-mediated immunity against the virulent form. An inactivated (killed) virus is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Zika virus (ZIKV): A member of the virus family Flaviviridae and the genus Flavivirus. Other members of this genus include dengue virus, yellow fever virus, Japanese encephalitis virus (JEV), West Nile virus and Spondweni virus. ZIKV is spread by the daytime-active mosquitoes *Aedes aegypti* and *A. albopictus*. This virus was first isolated from a Rhesus macaque from the Zika Forest of Uganda in 1947. Since the 1950s, ZIKV has been known to occur within a narrow equatorial belt from Africa to Asia. The virus spread eastward across the Pacific Ocean in 2013-2014, resulting in ZIKV outbreaks in Oceania to French Polynesia, New Caledonia, the Cook Islands, and Easter Island. In 2015, ZIKV spread to Mexico, Central America, the Caribbean and South America, where ZIKV has reached pandemic levels. Infection by ZIKV generally causes either no symptoms are mild symptoms, including mild headache, maculopapular rash, fever, malaise, conjunctivitis and joint pain. ZIKV causes symptoms in about 20% of infected individuals, and no deaths from the virus have yet been reported. However, ZIKV infection has been linked to the birth of microcephalic infants following maternal infection, as well an increase in cases of GBS. Reports have also indicated that ZIKV has the potential for human blood-borne and sexual transmission. ZIKV has also been found in human saliva and breastmilk. There are currently no available medical countermeasures for the treatment or prevention of Zika virus infection (Malone et al., *PLoS Negl Trop Dis* 10(3):e0004530, 2016).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Immunogens

Disclosed herein are immunogens that include, or consist of, non-naturally occurring fusion proteins. The fusion protein includes a Zika virus (ZIKV) envelope protein and a multimerization domain, and optionally a signal peptide. In these immunogens, the optional signal peptide can be a premembrane (prM) signal peptide, a mouse IgG signal peptide, and/or a human secretory signal peptide hidden Markov model. In these fusion proteins, the multimerization domain can be an immunoglobulin Fc domain, a T4 fibritin foldon trimerization domain, or a human collagen XV trimerization domain. Optionally, the fusion protein also can include a ZIKV prM protein. Optionally, the immunogen can include the fusion protein and another molecule, such as a carrier.

In several embodiments, the immunogens can be used to generate a neutralizing immune response to ZIKV in a subject, for example, to treat or prevent a ZIKV infection in the subject.

In some embodiments, the fusion protein includes, in N-terminal to C-terminal order, the signal peptide, the ZIKV envelope protein, and the multimerization domain. Optionally, the fusion protein includes the prM protein. In some embodiments, the fusion protein includes a prM protein between the signal peptide and the ZIKV envelope protein. In other embodiments, the fusion protein includes a prM protein between the ZIKV envelope protein and the multimerization domain.

In some embodiments, each domain within the fusion protein is consecutive. Thus, linker sequences are not included in the fusion protein.

However, in some embodiments, a linker protein can be utilized between two domains. Thus, a linker protein can be included 1) between the signal peptide and the ZIKV envelope protein, 2) between the ZIKV envelope protein and the multimerization domain; 3) between the signal peptide and a prM protein; 4) between the prM protein and the ZIKV envelope protein; 5) between the ZIKV envelope protein and the prM protein; and/or between the prM protein and the multimerization domain. A linker can be any amino acid sequence, but is generally 4 to 10 amino acids in length, such as 4 to 8 amino acids in length, or 4 to 6 amino acids in length. In some embodiments, the linker is 4, 5, or 6 amino acids in length. A linker can be, for example, QVQL (SEQ ID NO: 1); this linker can be included, for example, between the mouse IgG signal peptide and the ZIKV prM protein.

A. Signal Peptide

Optionally, the disclosed fusion proteins include a signal peptide, such as, but not limited to, at the N-terminal end of the immunogen. In some embodiments, the signal peptide is a premembrane (prM) signal peptide, a mouse IgG signal peptide, a human IgG signal peptide, or a human secretory signal peptide hidden Markov model. Signal peptides are typically located at the N-terminus of a polypeptide and are removed by signal peptidases after the polypeptide has crossed the membrane. Exemplary signal peptides include:

1. The human secretory signal peptide hidden Markov model (SEQ ID NO: 2)
MWWRLWWLLLLLLLLWPMVWA;

2. The signal peptide of mouse IgG (SEQ ID NO: 3)
MAVLGLLFCL VTFPSCVLS;

(Optionally, the linker QVQL (SEQ ID NO: 1) can be added at the end of this peptide, for cleavage of the signal peptide.)

3. The signal peptide of human IgG (SEQ ID NO: 4)
MEFGLSWVFLVALFRGVQC;

and (Optionally, the linker QVQL (SEQ ID NO: 1) can be added at the end of this peptide, for cleavage of the signal peptide.)

4. The premembrane (prM) signal peptide (SEQ ID NO: 5)
RGADTSVGIVGLLLTTAMAAEV.

A signal peptide can include an amino acid sequence at least 95% identical to one of SEQ ID NOs: 2, 3, 4 or 5, such as an amino acid sequence about 95%, about 96%, about 97%, about 98%, about 99% or 100% identical to one of SEQ ID NOs: 2, 3, 4 or 5, provided the signal peptide directs newly synthesized secretory or membrane proteins to and through membranes. A signal peptide can include at most 1, 2, 3, or 4 conservative amino acid substitutions in one of SEQ ID NOs: 2, 3, 4, or 5, provided the signal peptide directs newly synthesized secretory or membrane proteins to and through membranes. One of skill in the art can readily identify additional signal peptides of use.

B. ZIKV Envelope The disclosed immunogens include a ZIKV envelope protein. The envelope protein can be from any strain of ZIKV. In some embodiments, the envelope protein is expressed by a nucleic acid sequence that is codon-optimized for humans. Exemplary amino acid sequences, encoded by a nucleic acid sequences codon-optimized for human, are shown in SEQ ID NO: 6 and SEQ ID NO: 7.

In one embodiment, the envelope protein includes an amino acid sequence at least 95% identical to SEQ ID NO: 6, such as an amino acid sequence about 95%, about 96%, about 97%, about 98%, about 99% or 100% identical to SEQ ID NO: 6. In other embodiments, the envelope protein includes at most 1, 2, 3, 4 or 5 conservative amino acid substitutions in SEQ ID NO: 6.

(SEQ ID NO: 6)
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGS.

In additional embodiments, the envelope protein consists of an amino acid sequence at least 95% identical to SEQ ID NO: 6, such as an amino acid sequence about 95%, about 96%, about 97%, about 98%, about 99% or 100% identical to SEQ ID NO: 6. In other embodiments, the envelope protein consists of an amino acid sequence with at most 1, 2, 3, 4 or 5 conservative amino acid substitutions in SEQ ID NO: 6. In some non-limiting examples, the ZIKV envelope protein consists of the amino acid sequence of an amino acid sequence at least 95% identical to SEQ ID NO: 6, such as an amino acid sequence about 95%, about 96%, about 97%, about 98%, about 99% or 100% identical to SEQ ID NO: 6, wherein the immunogen also includes a prM protein (see below).

In another embodiment, the envelope protein includes an amino acid sequence at least 95% identical to SEQ ID NO: 7, such as an amino acid sequence about 95%, about 96%, about 97%, about 98%, about 99% or 100% identical to SEQ ID NO: 7. In other embodiments, the envelope protein includes at most 1, 2, 3, 4 or 5 conservative amino acid substitutions in SEQ ID NO: 7.

(SEQ ID NO: 7)
IRCIGVSNRDFVEGMSGGTWVDVVLEHGGCVTVMAQDKPTVDIELVTTYV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSL

This envelope protein includes the amino acid sequence of SEQ ID NO: 6, and additional amino acids (underlined in the sequence above; H region; stem/anchor region; ER retention signal).

In some embodiments, the envelope protein consists of an amino acid sequence at least 95% identical to SEQ ID NO: 7, such as an amino acid sequence about 95%, about 96%, about 97%, about 98%, about 99% or 100% identical to SEQ ID NO: 7. In other embodiments, the envelope protein consists of an amino acid sequence with at most 1, 2, 3, 4 or 5 conservative amino acid substitutions in SEQ ID NO: 7. In some non-limiting examples, the ZIKV envelope protein consists of the amino acid sequence of an amino acid sequence at least 95% identical to SEQ ID NO: 7, such as an amino acid sequence about 95%, about 96%, about 97%, about 98%, about 99% or 100% identical to SEQ ID NO: 7, and the immunogen also includes a prM protein (see below).

The envelope protein sequences provided as SEQ ID NO: 6 and SEQ ID NO: 7 are exemplary only. The ZIKV envelope protein can be from any ZIKV, including an African genotype strain or an Asian genotype strain. In some embodiments, the ZIKV is an African genotype strain, such as MR-766. In other embodiments, the ZIKV is an Asian genotype strain, such as SPH2015, PRVABC59, R103451, P6-740, FSS 13025 or R103451.

The ZIKV envelope protein can be from a wild type strain or an attenuated strain. ZIKV sequences are publicly available, see example GENBANK® Accession Nos. KU321639.1, KU955595.1, KU955594.1, KU955593.1, KU955592.1, KU955591.1, KU681082.3, KU681081.3 and KX247646.1, all of which are incorporated by reference as available on Dec. 30, 2016. In additional examples, the envelope protein is at least 90%, at least 95%, at least 96%, at least 97%, at least 98%, or at least 99% identical to a publicly available ZIKV sequence.

C. PrM

As discussed above, the disclosed immunogens include a ZIKV envelope protein. Optionally, the disclosed immunogens can also include a prM protein. In some embodiments, the ZIKV prM protein includes an amino acid sequence at least 95% identical to SEQ ID NO: 8, such as an amino acid sequence about 95%, about 96%, about 97%, about 98%, about 99% or 100% identical to SEQ ID NO: 8. In other embodiments, the ZIKV prM protein includes at most 1, 2, 3, 4 or 5 conservative amino acid substitutions in SEQ ID NO: 8.

(SEQ ID NO: 8)
TRRGSAYYMYLDRNDAGEAISFPTTLGMNKCYIQIMDLGHMCDATMSYEC

PMLDEGVEPDDVDCWCNTTSTWVVYGTCHHKKGEARRSRRAVTLPSHSTR

KLQTRSQTWLESREYTKHLIRVENWIFRNPGFALAAAAIAWLLGSSTSQK

VIYLVMILLIAPAYS

In some examples, the ZIKV prM protein consists of an amino acid sequence at least 95% identical to SEQ ID NO: 8, such as an amino acid sequence about 95%, about 96%, about 97%, about 98%, about 99% or 100% identical to SEQ ID NO: 8. In other embodiments, the prM protein consists of an amino acids sequence with at most 1, 2, 3, 4 or 5 conservative amino acid substitutions in SEQ ID NO: 8.

A linker sequence can be included between the Envelope Protein and the protein. However, in some embodiments, a linker sequence is not included between the envelope protein and the prM protein. In some embodiments, the linker sequence includes, or consists of, the amino acid sequence of SEQ ID NO: 1.

In some embodiments, the immunogen includes the envelope protein N-terminal to the prM protein. In other embodiments, the immunogen includes the prM protein N-terminal to the envelope protein.

The ZIKV prM protein can be from any ZIKV, including an African genotype strain or an Asian genotype strain. In some embodiments, the ZIKV is an African genotype strain, such as MR-766. In other embodiments, the ZIKV is an Asian genotype strain, such as SPH2015, PRVABC59, R103451, P6-740, FSS 13025 or R103451.

The ZIKV prM protein can be from a wild type strain or an attenuated strain. As noted above, ZIKV sequences are publicly available, see example GENBANK® Accession Nos. KU321639.1, KU955595.1, KU955594.1, KU955593.1, KU955592.1, KU955591.1, KU681082.3, KU681081.3 and KX247646.1, all of which are incorporated by reference as available on Dec. 30, 2016. In additional examples, the prM, and/or E protein is at least 90%, at least 95%, at least 96%, at least 97%, at least 98%, or at least 99% identical to a publicly available ZIKV sequence.

D. Multimerization Domain

The disclosed immunogens include a multimerization domain. In some embodiments, the multimerization domain is at the C-terminus of the immunogen. Suitable multimerization domains include, but are not limited to:

1. Immunoglobulin Dimerization Domain (SEQ ID NO: 9)
DKTHTCPSRPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVLHEALHSHYTQKSLSLSPGK

2. T4 Fibritin Foldon Trimerization Domain (SEQ ID NO: 10)
GYIPEAPRDGQAYVRKDGEWVLLSTFL;

and

3. Human Collagen XV Trimerization Domain (SEQ ID NO: 11)
VTAFSNMDDMLQKAHLVIEGTFIYLRDSTEFFIRVRDGWKKLQLGELIPI

PADSPPPPALSSNP.

A multimerization domain can include an amino acid sequence at least 95% identical to any one of SEQ ID NOs: 9, 10, or 11, such as an amino acid sequence about 95%, about 96%, about 97%, about 98%, about 99% or 100% identical to any one of SEQ ID NOs: 9, 10, or 11, provided the multimerization domain functions, such that dimers or trimers are produced (as appropriate to the native domain). A multimerization domain can include at most 1, 2, 3, or 4 conservative amino acid substitutions in one of any one of SEQ ID NOs: 9, 10, or 11, provided the multimerization domain functions, such that dimers or trimers are produced (as appropriate to the native domain). In some embodiments, the multimerization domain consists of the amino acid sequence of any one of SEQ ID NOs: 9, 10, or 11.

E. Carriers

In some embodiments, the immunogen can be another polypeptide, such as a carrier, in addition to the ZIKV fusion protein. An exemplary immunogen is shown below:

MAVLGLLFCLVTFPSCVLSQVQLTRRGSAYYMYLDRNDAGEAI

SFPTTLGMNKCYIQIMDLGHMCDATMSYECPMLDEGVEPDDVDCWCNTTS

TWVVYGTCHHKKGEARRSR

*RAVTLPSHSTRKLQTRSQTWLESREYTKHLI*

RVENWIFRNPGFALAAAAIAWLLGSSTSQKVIYLVMILLIAPAYSIRCIG

VSNRDFVEGMSGGTWVDVVLEHGGCVTVMAQDKPTVDIELVTTTVSNMAE

VRSYCYEASISDMASDSRCPTQGEAYLDKQSDTQYVCKRTLVDRGWGNGC

GLFGKGSLVTCAKFACSKKMTGKSIQPENLEYRIMLSVHGSQHSGMIVND

TGHETDENRAKVEITPNSPRAEATLGGFGSLGLDCEPRTGLDFSDLYYLT

MNNKHWLVHKEWFHDIPLPWHAGADTGTPHWNNKEALVEFKDAHAKRQTV

VVLGSQEGAVHTALAGALEAEMDGAKGRLSSGHLKCRLKMDKLRLKGVSY

SLCTAAFTFTKIPAETLHGTVTVEVQYAGTDGPCKVPAQMAVDMQTLTPV

GRLITANPVITESTENSKMMLELDPPFGDSYIVIGVGEKKITHHWHRSGS

DKTHTCPSRPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVLHEALHSHYTQKSLSLSPGK (SEQ ID NO: 12, a PreME sequence, in which the signal sequence (SEQ ID NO: 3) and the linker (SEQ ID NO: 1) are single underlined, the propeptide sequence is italicized, the matrix protein is bold (combined in SEQ ID NO: 8), the envelope protein (SEQ ID NO: 6) is double underlined, and the human IgG Fc dimerization domain (SEQ ID NO: 9) is plain text at the end of the molecule.

Examples of suitable carriers are those that can increase the immunogenicity of the conjugate and/or elicit antibodies against the carrier which are diagnostically and/or therapeutically beneficial. Useful carriers include semi-synthetic or synthetic materials containing one or more amino groups, such as those present in a lysine amino acid residue present in the carrier, to which a reactant moiety can be attached. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000). A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065); *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin (KLH), horseshoe crab hemocyanin, Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: Keyhole Limpet Hemocyanin (KLH), tetanus toxoid, diphtheria toxoid, or H influenza protein D (HiD) (for description of protein carriers for vaccines, see Pichichero, Protein carriers of conjugate vaccines: characteristics, development, and clinical trials., Hum Vaccin Immunother., 9: 2505-2523, 2013, which is incorporated by reference herein in its entirety). In other embodiments, the carrier is RS01, RS09 (or another TLR-4 agonist), fliC (or another flagellin).

III. Polynucleotides and Expression

Polynucleotides encoding a disclosed immunogen are also provided. These polynucleotides include DNA, cDNA and RNA sequences which encode the antigen. One of skill in the art can readily use the genetic code to construct a variety of functionally equivalent nucleic acids, such as nucleic acids which differ in sequence but which encode the same protein sequence, or encode a conjugate or fusion protein including the nucleic acid sequence. In some embodiments, the polynucleotide is codon optimized for expression in human cells. In specific non-limiting examples, nucleic acids encoding a PreMEFc, porcine teschovirus-1 2A, equine rhinitis virus 2A can be codon optimized.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

One exemplary nucleic acid sequence, encoding SEQ ID NO: 12, is provided below:

AAGCTTGCCACCATGGCCACCTCAGCAAGTTCCCACTTGAACAA

AGGCATCAAGCAAATGTACATGTCCCTGCCCCAGGGTGAGAAAGTCCAAG

CCATGTATATCTGGGTTGATGGTACCGGAGAAGGACTGCGCTGCAAAACC

CGCACCCTGGACTGTGAGCCCAAGTGTGTAGAAGAGTTACCTGAGTGGAA

TTTTGATGGCTCTAGTACCTTTCAGTCTGAGAGCTCCAACAGTGACATGT

ATCTCAGCCCTGTTGCCATGTTTCGGGACCCCTTCCGCAAAGAGCCCAAC

AAGCTGGTGTTCTGTGAAGTCTTCAAGTACAACCAGAAGCCTGCAGAGAC

CAATTTAAGACACACGTGTAAACGGATAATGGACATGGTGAGCAACCAGC

ACCCCTGGTTTGGAATGGAACAGGAGTATACTCTCTTGGGAACAGATGGG

CACCCTTTTGGTTGGCCTTCCGATGGCTTCCCTGGGCCCCAAGGTCTGTA

TTACTGTGGTGTGGGCGCAGACAAAGCCTATCGCAGGGATATCATGGAGG

CTCACTACCGTGCCTGCTTGTATGCTGGGGTCAAGATTACAGGAACATAT

GCTGAGGTCAAGCATGCCCAGTGGGAATTCCAAATAGGACCCTGTGAAGG

AATCCGCATGGGAGATCATCTCTGGGTGGCCCGTTTCATCTTGCATCGAG

TATGTAAAGACTTTGGAGTAATAGCAACCTTTGACTCCAAGCCCATTCCT

GGGAACTGGAATGGTGCAGGCTGCCATACCAACTTTAGTACCAAGACCAT

GCGGGAGGAGAATGGTCTGAAGCACATCAAGGAGGCCATTGAGAAACTAA

GCAAGCGGCACCGGTACCATATTCGAGCCTACGATCCCAAGGGGGGCTG

GACAATGCCCGTCGTCTGACTGGGTTCCACAAAACGTCCAACATCAACGA

CTTTTCAGCTGGCGTCGCCGATCGCAGTGCCAGCATCCGCATTCCCCGGA

CTGTCGGCCAGGAGAAGAAAGGTTACTTTGAAGCCCGCTGCCCCTCTGCC

-continued

AATTGTGACCCCTTTGCAGTGACAGAAGCCATCGTCCGCACATGCCTTCT

CAATGAGACTGGCGACCAGCCCTTCCAATACAAAAACGGCAGCGGCGCGA

CCAACTTTAGCCTCCTCAAGCAGGCGGGGGATGTGGAGGAGAACCCAGGT

CCTATGGTGAGCAAGGGCGAGGAGCTGTTCACCGGGGTGGTGCCCATCCT

GGTCGAGCTGGACGGCGACGTAAACGGCCACAAGTTCAGCGTGTCCGGCG

AGGGCGAGGGCGATGCCACCTACGGCAAGCTGACCCTGAAGTTCATCTGC

ACCACCGGCAAGCTGCCCGTGCCCTGGCCCACCCTCGTGACCACCCTGAC

CTACGGCGTGCAGTGCTTCAGCCGCTACCCCGACCACATGAAGCAGCACG

ACTTCTTCAAGTCCGCCATGCCCGAAGGCTACGTCCAGGAGCGCACCATC

TTCTTCAAGGACGACGGCAACTACAAGACCCGCGCCGAGGTGAAGTTCGA

GGGCGACACCCTGGTGAACCGCATCGAGCTGAAGGGCATCGACTTCAAGG

AGGACGGCAACATCCTGGGGCACAAGCTGGAGTACAACTACAACAGCCAC

AACGTCTATATCATGGCCGACAAGCAGAAGAACGGCATCAAGGTGAACTT

CAAGATCCGCCACAACATCGAGGACGGCAGCGTGCAGCTCGCCGACCACT

ACCAGCAGAACACCCCCATCGGCGACGGCCCCGTGCTGCTGCCCGACAAC

CACTACCTGAGCACCCAGTCCGCCCTGAGCAAAGACCCCAACGAGAAGCG

CGATCACATGGTCCTGCTGGAGTTCGTGACCGCCGCGGGATCACTCTCG

GCATGGACGAGCTGTACAAGGGCTCCGGCCAGTGTACAAACTACGCCCTG

CTTAAATTAGCCGGCGACGTGGAGTCAAACCCCGGCCCCGTCGAC<u>ATGGC</u>

<u>CGTTCTGGGTCTCCTGTTCTGCCTGGTCACATTCCCCAGTTGTGTGCTCA</u>

<u>GTCAGGTGCAGTTGACTAGGCGGGAAGCGCCTATTACATGTACCTGGAC</u>

<u>CGAAACGATGCCGGCGAAGCCATCTCCTTCCCCACCACGCTCGGAATGAA</u>

<u>CAAATGCTATATCCAGATCATGGATCTAGGGCACATGTGCGACGCGACCA</u>

<u>TGTCGTACGAGTGTCCCATGCTGGACGAAGGCGTTGAGCCTGACGACGTG</u>

<u>GACTGCTGGTGCAATACTACTAGCACTTGGGTGGTGTACGGGACCTGTCA</u>

<u>TCACAAGAAGGGCGAGGCCCGGCGCTCCCGTCGCGCAGTGACCCTGCCCT</u>

<u>CTCACTCAACCCGCAAGCTGCAGACTCGGTCGCAGACATGGCTGGAGTCC</u>

<u>CGGGAGTACACTAAGCACCTCATTCGCGTGGAGAACTGGATCTTCCGCAA</u>

<u>CCCCGGGTTTGCTCTCGCCGCCGCTGCCATCGCGTGGCTGTTAGGAAGTT</u>

<u>CCACGTCCCAGAAAGTGATCTACCTGGTTATGATCCTCCTTATCGCCCCC</u>

<u>GCCTACTCCATCCGCTGTATTGGGGTGAGTAACCGCGACTTCGTGGAGGG</u>

<u>GATGTCCGGCGGCACCTGGGTGGATGTGGTGCTGGAGCACGGGGGCTGTG</u>

<u>TGACGGTCATGGCGCAAGACAAGCCTACCGTGGATATCGAGCTCGTGACC</u>

<u>ACAACCGTGTCCAACATGGCAGAGGTCCGGTCCTATTGCTATGAAGCCAG</u>

<u>TATCTCTGACATGGCCAGCGACAGTCGCTGCCCGACGCAGGGGAGGCCT</u>

<u>ATCTCGACAAGCAGTCGGATACCCAATACGTGTGTAAGCGGACTCTCGTG</u>

<u>GACCGAGGCTGGGCAACGGCTGCGGCCTGTTCGGAAAGGGCAGCCTCGT</u>

<u>AACTTGCGCCAAGTTCGCGTGCTCTAAGAAGATGACCGGTAAGAGTATCC</u>

<u>AGCCGGAGAACCTGGAATACAGGATCATGCTCTCGGTGCACGGCTCCCAG</u>

<u>CACTCCGGCATGATCGTTAACGACACCGGCCACGAAACCGATGAGAACCG</u>

<u>CGCTAAGGTGGAGATCACCCCAAACTCCCCCCGGGCGGAGGCTACCCTGG</u>

-continued

GCGGGTTCGGGTCGCTCGGGCTCGACTGTGAGCCCAGGACCGGCCTGGAT

TTCTCGGATCTGTACTACCTGACCATGAATAATAAGCACTGGCTGGTGCA

CAAGGAGTGGTTCCACGACATCCCGTTACCCTGGCACGCAGGCGCCGACA

CCGGGACACCTCACTGGAACAACAAGGAGGCCTTAGTCGAGTTCAAGGAT

GCCCACGCCAAACGGCAGACCGTGGTGGTGTTAGGCTCCCAGGAAGGGGC

CGTGCACACCGCCCTGGCCGGTGCCCTGGAGGCCGAGATGGATGGCGCCA

AAGGCCGCCTGTCATCCGGACACCTGAAGTGCCGCCTCAAGATGGACAAG

TTGAGGCTGAAGGGGGTGTCTTATTCGCTGTGTACCGCAGCCTTCACGTT

CACAAAGATCCCAGCCGAGACACTGCACGGGACCGTCACCGTGGAGGTTC

AGTACGCCGGGACCGACGGGCCGTGCAAGGTTCCCGCCCAGATGGCAGTG

GACATGCAGACCCTGACACCAGTCGGCCGACTCATTACGGCCAACCCAGT

CATCACCGAGTCCACGGAGAACTCCAAGATGATGCTCGAACTGGACCCCC

CTTTCGGTGACAGTTACATCGTGATCGGCGTGGGCGAAAAGAAGATCACT

CACCACTGGCATCGGTCAGGATCCGACAAGACTCATACCTGTCCATCGCG

CCCTTGCCCCGCCCCGAGCTCCTTGGCGGTCCATCCGTGTTCCTGTTTC

CACCAAAGCCGAAAGATACCCTGATGATCTCCCGGACCCCCGAGGTGACC

TGCGTGGTGGTGGACGTGAGTCACGAGGACCCCGAGGTGAAGTTCAACTG

GTACGTCGATGGGGTCGAGGTGCACAACGCGAAGACGAAGCCAAGGGAGG

AGCAGTACAACTCCACCTACAGGGTGGTCTCGGTTCTCACCGTCCTGCAC

CAGGACTGGCTGAATGGCAAGGAGTACAAGTGCAAGGTGTCGAACAAGGC

ACTGCCCGCACCAATCGAAAAGACAATATCCAAGGCAAAAGGACAGCCGA

GAGAGCCCCAGGTGTATACCCTGCCCCCGTCGCGAGACGAGCTGACCAAG

AATCAGGTGAGTCTGACGTGCCTGGTGAAGGGCTTTTATCCCAGCGACAT

CGCTGTGGAATGGGAGAGTAATGGCCAGCCCGAGAACAACTATAAGACCA

CCCCTCCCGTCCTGGATTCGGATGGGAGTTTCTTCCTGTACTCGAAGCTC

ACTGTCGATAAGTCCCGGTGGCAGCAGGGGAACGTGTTTTCCTGCTCCGT

TCTGCACGAAGCGCTGCATTCGCACTACACCCAGAAATCGCTTAGTCTCT

CCCCCGGCAAGTAAGCGGCCGCCTCGAG (SEQ ID NO: 13, wherein the nucleic acid sequence encoding the PreMEFc antigenic sequence is underlined, beginning a nucleotide 1,990).

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed immunogen can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed immunogen can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed immunogen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4$^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using an adenoviral vector, as discussed below.

Modifications can be made to a nucleic acid encoding a disclosed immunogen without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

IV. Viral Vectors

A nucleic acid molecule encoding a disclosed immunogen can be included in a viral vector, for example, for expression of the immunogen in a host cell, or for immunization of a subject as disclosed herein. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed immunogens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed immunogen. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009) or an Ad5 vector is used (see the Examples Section). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/022311.

V. Microneedle Arrays (MNAs)

The disclosed immunogens, and vectors encoding these immunogens, can be administered in microneedle array, see, for example, U.S. Published Patent Application No. US-2016-0271381-A1, which is incorporated herein by reference. In some embodiments, the microneedle array is a tip-loaded microarray, which can be prepared using micro-milled master molds and spin-molds, see U.S. Published Patent Application No. US-2016-0271381-A1.

Dissolvable microneedle arrays enable efficient and safe drug and vaccine delivery to the skin and mucosal surfaces. However, inefficient drug delivery can result from the homogenous nature of conventional microneedle array fabrication. Although the drugs or other cargo that is to be delivered to the patient are generally incorporated into the entire microneedle array matrix, in practice only the microneedles enter the skin and therefore, only cargo contained in the volume of the individual needles is deliverable. Accordingly, the vast majority of the drugs or other cargo that is localized in the non-needle components (e.g., the supporting structure of the array) is never delivered to the patient and is generally discarded as waste.

A fully-dissolvable microneedle array substrate and unique microneedle geometries can be utilized that enable effective delivery of the immunogens, and vectors encoding the disclosed immunogens. This technology can also uniquely enable the simultaneous co-delivery of multiple chemically distinct agents for polyfunctional drug delivery. Examples of the utility of these devices include, for example, (1) simultaneous delivery of the disclosed immunogens and optionally adjuvants to generate a polyvalent immune response relevant to ZIKV disease prevention and (2) localized skin delivery.

In some embodiments, provided herein is a dissolvable microneedle array for transdermal insertion, e.g., local cutaneous delivery, into a subject for promoting an immune response against Zika virus (ZIKV) in a subject in need thereof. The array includes a base portion and a plurality of microneedles extending from the base portion and containing a disclosed immunogen, or a vector encoding the immunogen, and optionally at least one adjuvant.

In further embodiments, the plurality of microneedles are pre-formed to have a shape that comprises a first cross-sectional dimension at a top portion, a second cross-sectional dimension at a bottom portion, and a third cross-sectional dimension at an intermediate portion, wherein the intermediate portion is located between the top portion and the bottom portion, and the third cross-sectional dimension is greater than the first and second cross-sectional dimensions.

In yet other embodiments, each microneedle comprises a plurality of layers of dissoluble biocompatible material, such as, but not limited to carboxymethylcellulose.

In some embodiments, a fabrication technology is utilized that results in various active components to be incorporated into the needle tips, see U.S. Published Patent Application No. US-2016-0271381-A1, which is incorporated herein by reference. Thus, by localizing the active components in this manner, the remainder of the microneedle array volume includes less expensive matrix material that is non-active and generally regarded as safe. The net result is greatly improved efficiency of drug delivery based on (1) reduced waste of non-deliverable active components incorporated into the non-needle portions of the microneedle array, and (2) higher drug concentration in the skin penetrating needle tips.

Thus, in some embodiments, the active component is concentrated in the microneedle tips of the respective arrays. Thus, in contrast to conventional microneedle arrays, the active component is not present at even concentration throughout the microneedle array since there is little or no active component present in the supporting base structure. In addition, in some embodiments (as shown, for example, in FIGS. 3A, 3B, 4A, and 4B of U.S. Published Patent Application No. US-2016-0271381-A1, which is incorporated herein by reference), not only is there little or no active component in the supporting structures, the location of the active component is concentrated in the upper half of the individual microneedles in the array. In some embodiments, the active component concentrated in the upper half of the individual microneedles. The active component is concentrated in the tip of the microneedle, with the tip being defined by an area of the microneedle that extends from a base portion in a narrowing and/or tapered manner. The base portion, in turn, extends from the supporting structure of the array.

As noted above, in some embodiments, individual microneedles can comprise active components only in the upper half of the microneedle. In other embodiments, individual microneedles can comprise active components only in the tips or in a narrowing portion near the tip of the microneedle. In still other embodiments, individual needles can comprise active components throughout the entire microneedle portion that extends from the supporting structure, see U.S. Published Patent Application No. US-2016-0271381-A1, which is incorporated herein by reference.

The disclosed immunogens can also be delivered as disclosed in PCT Application No. PCT/US2016/057363, which is incorporated herein by reference. This PCT application disclosed microneedle arrays that can be configured to penetrate the stratum corneum to deliver their cargo (e.g., biologics or bioactive components) to the epidermis and/or dermis, while minimizing pain and bleeding by preventing penetration to deeper layers that may contain nerve endings and vessels. Pyramidal CMC-microneedles effectively penetrated the stratum corneum, epidermis, and dermis of living human skin, and thus can be used for cutaneous delivery. Thus, in some embodiments, the microneedle array includes pyradmidal CMC-microneedles.

To construct the microneedle arrays, a base material can be used to form portions of each microneedle that have bioactive components and portions that do not. As discussed above, each microneedle can comprise bioactive components only in the microneedles, or in some embodiments, only in the upper half of the microneedles, or in other embodiments, only in a portion of the microneedle that tapers near the tip. Thus, to control the delivery of the bioactive component(s) and to control the cost of the microneedle arrays, each microneedle preferably has a portion with a bioactive component (immunogen and/or adjuvant) and a portion without a bioactive component. In the embodiments described herein, the portion without the bioactive component includes the supporting structure of the microneedle array and, in some embodiments, a base portion (e.g., a lower half) of each microneedle in the array.

Various materials can be used as the base material for the microneedle arrays. The structural substrates of biodegradable solid microneedles most commonly include poly(lactic-co-glycolic acid) (PLGA) or carboxymethylcellulose (CMC) based formulations; however, other bases can be used.

CMC is generally preferable to PLGA as the base material of the microneedle arrays described herein. The PLGA based devices can limit drug delivery and vaccine applications due to the relatively high temperature (e.g., 135 degrees Celsius or higher) and vacuum required for fabrication. In contrast, a CMC-based matrix can be formed at room temperature in a simple spin-casting and drying process, making CMC-microneedle arrays more desirable for incorporation of sensitive biologics, peptides, proteins, nucleic acids, and other various bioactive components.

CMC-hydrogel can be prepared from low viscosity sodium salt of CMC with or without active components (as described below) in sterile $dH_2O$. In the exemplary embodiment, CMC can be mixed with sterile distilled water ($dH_2O$) and with the active components to achieve about 25 wt % CMC concentration. The resulting mixture can be stirred to homogeneity and equilibrated at about 4 degrees Celsius for 24 hours. During this period, the CMC and any other components can be hydrated and a hydrogel can be formed. The hydrogel can be degassed in a vacuum for about an hour and centrifuged at about 20,000 g for an hour to remove residual micro-sized air bubbles that might interfere with a spincasting/drying process of the CMC-microneedle arrays. The dry matter content of the hydrogel can be tested by drying a fraction (10 g) of it at 85 degrees Celsius for about 72 hours. The ready-to-use CMC-hydrogel is desirably stored at about 4 degrees Celsius until use.

Active components, such as a disclosed immunogen or a vector encoding the immunogen, and optionally an adjuvant, can be incorporated in a hydrogel of CMC at a relatively high (20-30%) CMC-dry biologics weight ratio before the spin-casting process. Arrays can be spin-cast at room temperature, making the process compatible with the functional stability of a structurally broad range of bioactive components. Since the master and production molds can be reusable for a large number of fabrication cycles, the fabrication costs can be greatly reduced. The resulting dehydrated CMC-microneedle arrays are generally stable at room temperature or slightly lower temperatures (such as about 4 degrees Celsius), and preserve the activity of the incorporated biologics, facilitating easy, low cost storage and distribution.

In an exemplary embodiment, the surface of the production molds can be covered with about 50 μl (for molds with 11 mm diameter) of CMC-hydrogel and spin-casted by centrifugation at 2,500 g for about 5 minutes. After the initial CMC-hydrogel layer, another 50 μl CMC-hydrogel can be layered over the mold and centrifuged for about 4 hours at 2,500 g. At the end of a drying process, the CMC-microneedle arrays can be separated from the molds, trimmed off from excess material at the edges, collected and stored at about 4 degrees Celsius. The production molds can be cleaned and reused for further casting of microneedle arrays.

In some embodiments, CMC-solids can be formed with layers that do not contain active components and layers that contain active components. FIGS. 11A-D of PCT Application No. PCT/US2016/057363, incorporated herein by reference) illustrate CMC-solids with different shapes (FIGS. 11A and 11B of PCT Application No. PCT/US2016/057363) and embedded active cargos on an upper layer which becomes, after micromilling, the portions of the microneedle with the active components. FIGS. 12A and 12B of PCT/US2016/057363, also illustrate CMC-solids with different shapes, with FIG. 12B showing a square shape and FIG. 12B showing a rectangular shape. Both CMC solids can be milled to dimensions for further processing as described herein. It should be understood that the geometries are not intended to be limiting. Any geometry can be used with the immunogens and vectors disclosed herein.

V. Pharmaceutical Compositions and Methods for Eliciting an Immune Response

Provided herein are methods of eliciting an immune response in a subject by administering to the subject an immunogen, or a vector encoding the immunogen, as disclosed herein. In a particular example, the subject is a human. The immunogen, or a viral vector encoding the immunogen, is used, for examples, to produce an immune response that prevents or inhibits infection with a ZIKV. The subject can be a human.

In some examples, the method further includes selecting a subject in need of enhanced immunity to ZIKV. Subjects in need of enhanced immunity to ZIKV include subjects who are at risk of ZIKV infection, subjects who have been exposed to one or more ZIKV, and subjects who have previously been vaccinated with ZIKV or other flavivirus vaccines. Residents of, or travelers to, countries or regions where ZIKV is endemic are at risk of contracting ZIKV. Additional factors that contribute to risk of infection with ZIKV include the characteristics of the location, presence of ZIKV in the area, exposure to mosquitos, and lack of preventive measures (such as insect repellant). The subject can be female, such as a human of child-bearing age.

One or more of the disclosed immunogens, or vectors encoding the immunogens, are administered to a subject by any of the routes normally used for introducing a composition into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

In some embodiments, the immunogen, or a vector encoding the immunogen, is administered using a microneedle array. Thus, the immunogen, or the vector encoding the immunogen, can be administered to the subcutaneous microenvironment of a subject of interest.

Immunogenic compositions are administered in any suitable manner, such as with pharmaceutically acceptable carriers. Pharmaceutically acceptable carriers are determined in part by the particular composition being administered, as well as by the particular method used to administer the composition. See, e.g., *Remington: The Science and Practice of Pharmacy*, The University of the Sciences in Philadelphia, Editor, Lippincott, Williams, & Wilkins, Philadelphia, Pa., $21^{st}$ Edition (2005). Accordingly, there is a wide variety of suitable formulations of pharmaceutical compositions of the present disclosure.

The composition can include an adjuvant. In some embodiments, the adjuvant is a cyclic dinucleotide, such as, but not limited to, 2'3'-cGAMP (cyclic [G(2',5')pA(3',5')p]). However, any adjuvant can be utilized.

The immunogenic compositions may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In some examples, the compositions disclosed herein include one or more adjuvants. In other examples, an adjuvant is not included in the composition, but is separately administered to a subject (for example, in combination with a composition disclosed herein) before, after, or substantially simultaneously with administration of one or more of the compositions disclosed herein. Adjuvants are agents that increase or enhance an immune response in a subject administered an antigen, compared to administration of the antigen in the absence of an adjuvant. One example of an adjuvant is an aluminum salt, such as aluminum hydroxide, aluminum phosphate, aluminum potassium sulfate, or aluminum hydroxyphosphate. Other adjuvants include biological adjuvants, such as cytokines (for example, IL-2, IL-6, IL-12, RANTES, GM-CSF, TNF-α, or IFN-γ), growth factors (for example, GM-CSF or G-CSF), one or more molecules such as OX-40L or 4-1 BBL, immunostimulatory oligonucleotides (for example, CpG oligonucleotides), Toll-like receptor agonists (for example, TLR2, TLR4, TLR7/8, or TLR9 agonists), and bacterial lipopolysaccharides or their derivatives (such as 3D-MPL). Additional adjuvants include oil and water emulsions, squalene, or other agents. In one example, the adjuvant is a mixture of stabilizing detergents, micelle-forming agent, and oil available under the name PROVAX® (IDEC Pharmaceuticals, San Diego, Calif.). One of skill in the art can select a suitable adjuvant or combination of adjuvants to be included in the compositions disclosed herein or administered to a subject in combination with the compositions disclosed herein.

A non-limiting range for a therapeutically effective amount of the disclosed immunogen within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example, 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen such as from about 1-300 μg, for example, a dosage of about 1, 2, 3, 4, 5, 6, 7, 8, 9, 10, 15, 20, 30, 40, 50, 60, 70, 80, 90, 100, 150, 200, 250, or about 300 μg.

Dosage can be varied by the attending clinician to maintain a desired concentration at a target site (for example, systemic circulation). Higher or lower concentrations can be selected based on the mode of delivery, for example, transepidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response. A therapeutically effective amount is also one in which any toxic or detrimental side effects of the disclosed immunogen and/or other biologically active agent is outweighed in clinical terms by therapeutically beneficial effects.

A nucleic acid molecule or viral vector can be administered. One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, a disclosed fusion protein can be expressed by attenuated viral hosts or vectors or bacterial vectors. Recombinant vaccinia virus, adenovirus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus Calmette Guerin*) provides another vector for expression of the peptides (see Stover, *Nature* 351:456-460, 1991).

In one embodiment, a nucleic acid encoding a disclosed fusion protein is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

Administration is accomplished by single or multiple doses. The dose administered to a subject in the context of the present disclosure should be sufficient to induce a beneficial therapeutic response in a subject over time, or to inhibit or prevent ZIKV infection. The dose required will vary from subject to subject depending on the species, age, weight and general condition of the subject, the severity of the infection being treated, the particular immunogenic composition being used, and its mode of administration. An appropriate dose can be determined by one of ordinary skill in the art using only routine experimentation.

The volume of administration will vary depending on the route of administration. By way of example, intramuscular injections may range from about 0.1 ml to about 1.0 ml. Those of ordinary skill in the art will know appropriate volumes for different routes of administration.

Repeated immunizations may be necessary to produce an immune response in a subject. When administered in multiple doses, the booster doses are administered at various time intervals, such as weeks or months to years. In other examples, the a one or more of the disclosed immunogens, or one or more vectors encoding a disclosed immunogen are used as a booster following administration of one or more ZIKV vaccines. In one example, a subject is administered a prime dose of a ZIKV vaccine followed by at least one boost dose of an immunogen, or a vector encoding the immunogen, as disclosed herein. In alternative examples, the immunogen, or the vector encoding the immunogen is administered first, followed by a booster administration of another ZIKV vaccine, such as an inactivated ZIKV vaccine.

In some embodiments, a prime boost strategy is utilized. In some examples, the boost dose is administered about 14, 30, 60, 90, or more days after administration of the prime dose. Additional boosters can be administered at subsequent time points, if determined to be necessary or beneficial. Immunization protocols (such as amount of immunogen, number of doses and timing of administration) can be determined experimentally, for example by using animal models (such as mice or non-human primates), followed by clinical testing in humans.

In some non-limiting examples, initial injections may range from about 1 µg to about 1 mg, with some embodiments having a range of about 10 µg to about 800 µg, and still other embodiments a range of from about 25 µg to about 500 µg. Following an initial administration of the immune stimulatory composition, subjects may receive one or several booster administrations, adequately spaced. Booster administrations may range from about 1 µg to about 1 mg, with other embodiments having a range of about 10 µg to about 750 µg, and still others a range of about 50 µg to about 500 µg. Periodic boosters at intervals of 1-5 years, for instance three years, may be desirable to maintain the desired levels of protective immunity.

In some embodiments, following immunization, the immune response can be assessed. In some non-limiting examples, a biological sample can be obtained from the subject, and antibodies and/or reactive T cells specific for ZIKV can be assessed.

The following examples are provided to illustrate certain particular features and/or embodiments. These examples should not be construed to limit the disclosure to the particular features or embodiments described.

EXAMPLES

Example 1

Materials & Methods

Adenoviral Construction and Purification of Recombinant Protein:

For construction of pAd/ZIKV-Efl, the gene encoding human secretory signal peptide hidden Markov model (SP-HMM, MWWRLWWLLLLLLLLWPMVWA (SEQ ID NO: 1)), the extracellular portion of the ZIKV strain BeH815744 envelope gene (GENBANK® Accession No. KU365780, defined as amino acids 216-794 of the polyprotein, incorporated by reference herein), BamH I-linked T4 fibritin foldon trimerization domain (GSGYIPEAPRDGQAYVRKDGEWVLLSTFL (SEQ ID NO: 2)), Tobacco Etch Virus Protease (Tp) (ENLYFEG (SEQ ID NO: 3)), and six histidine tag were codon-optimized for optimal expression in mammalian cells using the UpGene codon optimization algorithm (Gao et al., 2004, Biotechnol Prog, 20, 443-8). pAd/ZIKV-Efl was generated by subcloning the codon-optimized ZIKV-Efl gene into the shuttle vector, pAd (GENBANK® Accession No. U62024) at SalI/NotI sites. Subsequently, replication-defective adenovirus 5, designated as AdS.ZIKV-Efl, was generated by loxP homologous recombination. Moreover, purified recombinant proteins named ZIKV-rEfl were also purified from the supernatant using His60 Ni Superflow Resin (Clontech) under native conditions to be used as a subunit vaccine. Briefly, the supernatant of Human Embryonic Kidney (HEK) 293 cells infected with Ad5.ZIKV-Efl was heat-inactivated at 65° C. for 30 min and mixed with the same volume of binding buffer (40 mM imidazole, 900 mM NaCl, 100 mM sodium phosphate, pH 7.4). His60 Ni Superflow Resin (Clontech) previously equilibrated with equilibration buffer (20 mM imidazole, 500 mM NaCl, 50 mM sodium phosphate, pH 7.4) was added and the mixture was incubated overnight at 4° C. with rotation. The next day, the settled resin mix was packed into an empty column. The column was washed with 10 ml of equilibration buffer three times followed by 10 ml of wash buffer (40 mM imidazole, 500 mM NaCl, 50 mM sodium phosphate, pH 7.4) three times and eluted in 10 ml of elution buffer (500 mM imidazole, 500 mM NaCl, 50 mM sodium phosphate, pH 7.4). The eluate was concentrated and desalted with phosphate buffered saline (PBS) in an Amicon Ultra-15 filter (Millipore). This desalting step was repeated three times. The concentrations of the purified recombinant ZIKV-Efl were determined by the Bradford assay using bovine serum albumin (BSA) as a protein standard.

Virus Stock:

ZIKV stocks were obtained from the University of Texas Medical Branch. Vero cells were infected with ZIKV DAKAR41542 at MOI of 0.01 and incubated until the monolayer showed significant cytopathic effect. Culture supernatant was clarified by centrifugation at 3,000 g for 15 min. Virus was precipitated overnight by addition of NaCl (0.4M) and 6% polyethylene glycol. After centrifugation at 10,000 g for 30 min, the viral pellet was re-dissolved to 1/100 of the original volume in PBS and centrifuged on a 5 to 50% sucrose gradient at 90,000 g for 3 h, followed by dialysis with PBS buffer. The virus was diluted to a proper concentration with 5% Trehalose Buffer (20 mM Tris, pH 7.8, 75 mM NaCl, 2 mM $MgCl_2$, 5% Trehalose, 0.0025% Tween 80) and kept at −80° C. For the virus titer, vero cells were seeded in a six-well plate at $1 \times 10^5$ cells per well. The next day, cells were infected with log dilutions of ZIKV for 1 h and overlayed with 1% methyl cellulose media containing 5% fetal bovine serum. After three days of infection, cells were stained with 1% crystal violet. Plaques were counted and titers were calculated by multiplying the number of plaques by the dilution and dividing by the infection volume.

Animal Experiments:

Six- to eight-week-old C57BL/6 female mice (five animals per group) were inoculated subcutaneously (s.c.) with $1 \times 10^{11}$ viral particles (v.p.) of AdS.ZIKV-Efl or PBS as a negative control, and intradermally (i.d.) with MNA coated with 20 µg of ZIKV-rEfl. Two weeks after the primary immunization, mice were boosted intranasally (i.n.) or i.d. with the same dose of the respective immunogens. Mice were bled from the retro-orbital sinus at week 0, 2, 4, and 6, and serum samples were evaluated for ZIKV antibody by enzyme-linked immunosorbent assay (ELISA) and plaque reduction neutralization assay (PRNT).

To evaluate passive protection by maternal antibody, pups were obtained by mating non-immunized males with immunized females at three weeks following booster vaccination. Pups were challenged intraperitoneally (i.p.) with ZIKV DAKAR41542 ($10^5$ pfu/50 µl) at seven days after birth. Two non-challenged pups from each litter were used as a control and bled at 28 days after birth to determine passive maternal antibodies. The physical condition of the pups was observed and their body weights were measured daily for 15 days. Exhibiting >10% loss of body weight was defined as onset of disease. In addition to mice that were found dead, mice with weight loss exceeding 25% of their highest body weight were euthanized and recorded as dead. Severity of neurological signs was scored as described previously (Yoshii et al., 2014, J Virol, 88, 5406-20). Signs of paralysis and loss of balance associated with viral infection were scored as 0 (absent), 1 (present), or 2 (severe). Scoring for paralysis was assigned as follows: 0, normal; 1, dragging limbs or inversion of dorsum pedis; and 2, complete paralysis and no spontaneous movement. Scoring for loss of balance was assigned as follows: 0, normal; 1, leaning of head or trunk posture to one side; and 2, inability to retain posture and falling to one side or a circling movement to one side. Total scores were quantified and were expressed as means±the standard errors of the mean.

ELISA Assay:

Sera from the animals were collected every two weeks and tested for ZIKV-specific IgG by conventional ELISA. Briefly, ELISA plates were coated with $2\times10^5$ pfu of heat-inactivated ZIKV DAKAR4542 at 60° C. for 20 minutes per well overnight at 4° C. in carbonate coating buffer (100 mM, pH 9.5) and then blocked with PBS containing 0.05% Tween 20 (PBS-T) and 2% BSA for one hour. Mouse sera were diluted 1:200 or 1:20 for pups sera in PBS-T with 1% BSA and incubated for two hours. After the plates were washed, HRP-conjugated anti-mouse IgG (1:2000, Santacruz) was added to each well and incubated for one hour. The plates were washed three times and developed with 3,3'5,5'-tetramethylbenzidine, and the reaction was stopped with 1M $H_2SO_4$ and absorbance at 450 nm was determined using an ELISA reader (BIO-TEK instruments).

Plaque Reduction Neutralization Assay (PRNT):

To determine the plaque reduction neutralizing titer at week 6, 60 μl of the pooled sera or 30 μl of each mouse sera was diluted in twofold serial dilutions (from 1/16 to 1/516 or from 1/32 to 1/1024) and incubated with 100 pfu of ZIKV DAKAR41542 in 100 μl of serum-free media at 37° C. for 1 h and subsequently added to a Vero cell monolayer at a density of $5\times10^4$ cells grown in six-well tissue culture plates and further incubated at 37° C. for 1 h. After incubation, the inoculant was removed, the semisolid media was added, and the plates were incubated for an additional five days. Titers were expressed as the reciprocal of the highest serum dilution still giving a 50% reduction in plaque number ($PRNT_{50}$) relative to samples incubated with pre-immunized control pooled sera.

Statistical Analysis:

In vitro experiments in this paper were repeated at least twice and data shown are means of those replicates ±standard error. For the statistical analysis, the Student's t-test, one-way analysis of variance and Tukey's multiple comparison tests, and log-rank (Mantel-Cox) test were performed using Graph Pad Prism version 5.0 software (San Diego, Calif., USA). Results were considered statistically significant when the p value was <0.05. Symbols *, , and * are used to indicate p values of <0.05, <0.01, and <0.001, respectively.

Example 2

Production and Testing

Recombinant E1/E3-deleted adenovirus serotype 5-based vectors were generated that encode for the human secretory signal peptide hidden Markov model (SP-HMM) followed by the codon-optimized extracellular portion of the ZIKV BeH815744 E gene fused to the T4 fibritin foldon trimerization domain (ZIKV-Efl). Moreover, the ZIKV-Efl antigen was engineered with a polyhistidine-tag and a Tobacco Etch Virus (TEV) protease cleavage sequence to facilitate downstream purification (FIG. 1). The replication-defective adenovirus 5, designated as Ad5.ZIKV-Efl, was generated by loxP homologous recombination as previously described (Kim et al., 2014, J Virol, 88, 5100-8; Hardy et al., 1997, J Virol, 71, 1842-9). Recombinant ZIKV-rEfl protein was purified from the supernatant of a Ad5.ZIKV-Efl-infected HEK 293 cell line using His60 Ni Superflow Resin under native conditions and packaged as a subunit vaccine in an MNA (MNA-ZIKV-Efl).

Figure 2A:
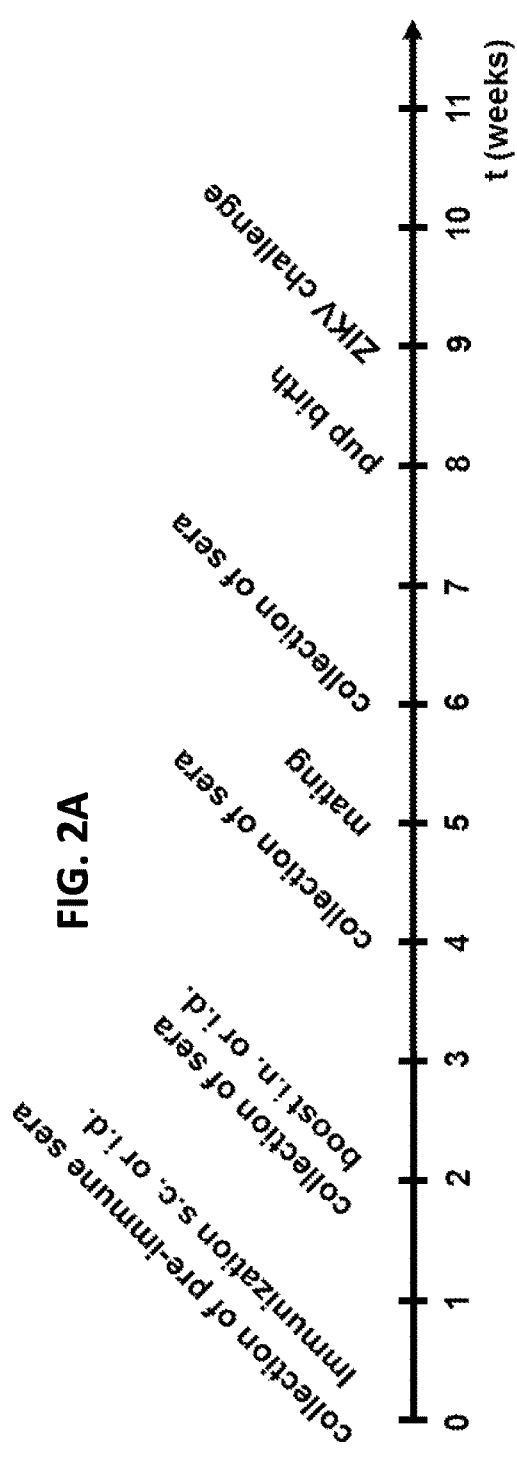
FIGS. 2A-2C. Characterization of ZIKV-specific immune responses induced by AdS.ZIKV-Efl and MNA-ZIKV-rEfl.
Figure 2B:
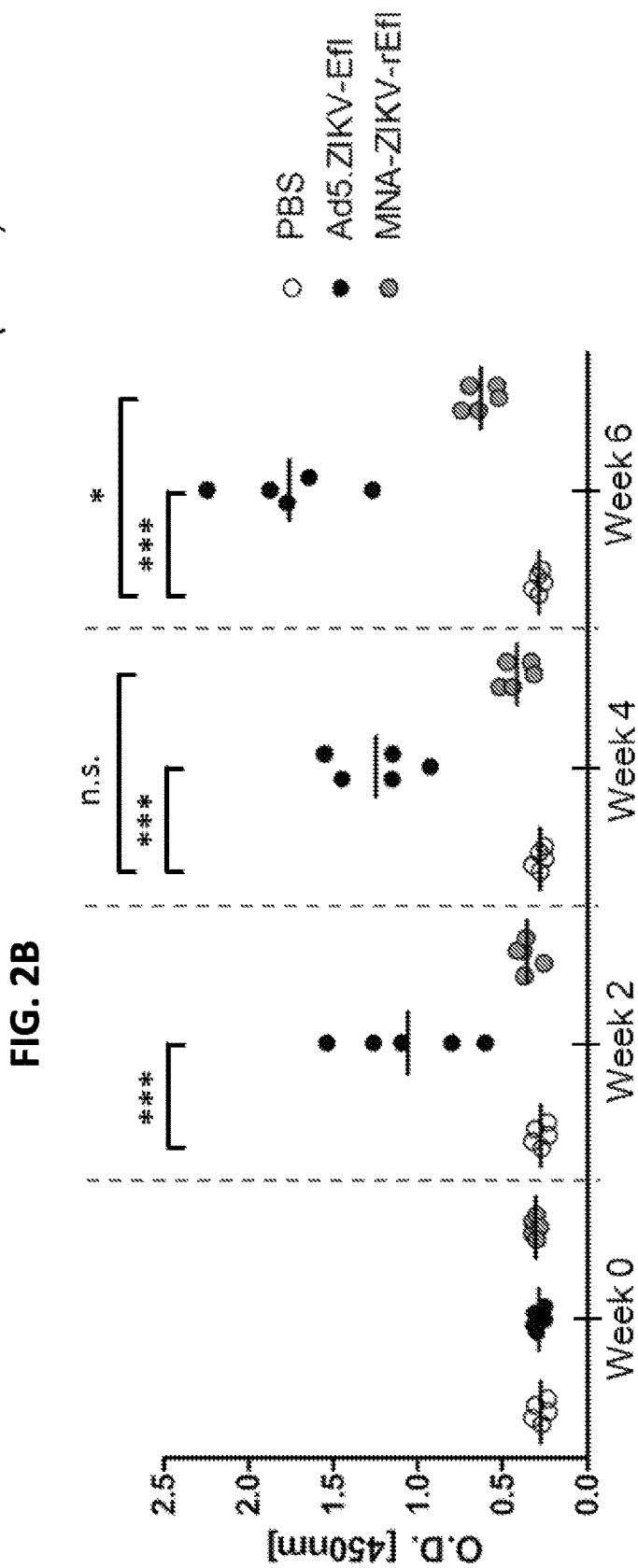

The ability of AdS.ZIKV-Efl and MNA-ZIKV-rEfl to elicit a specific anti-ZIKV immune response was tested in vivo. C57BL/6 mice were inoculated s.c. with 1011vp of Ad5.ZIKV-Efl or i.d. with 20 ug of MNA-ZIKV-rEfl, or with PBS on day 0 followed by booster immunization on day 14 with the same dose i.n. or i.d., respectively (FIG. 2a). At 0, 2, 4, and 6 weeks post prime immunization, sera were obtained from all mice and screened for the presence of ZIKV-specific antibodies using ELISA analysis. ZIKV-specific antibodies were detected as soon as two weeks after the first immunization in the sera of mice vaccinated with AdS.ZIKV-Efl (P=0.0002), while mice immunized MNA-ZIKV-rEfl showed significant titers at four weeks after the booster immunization (P<0.05) when compared with the sera of mice immunized with PBS (FIG. 2b).

Figure 2C:
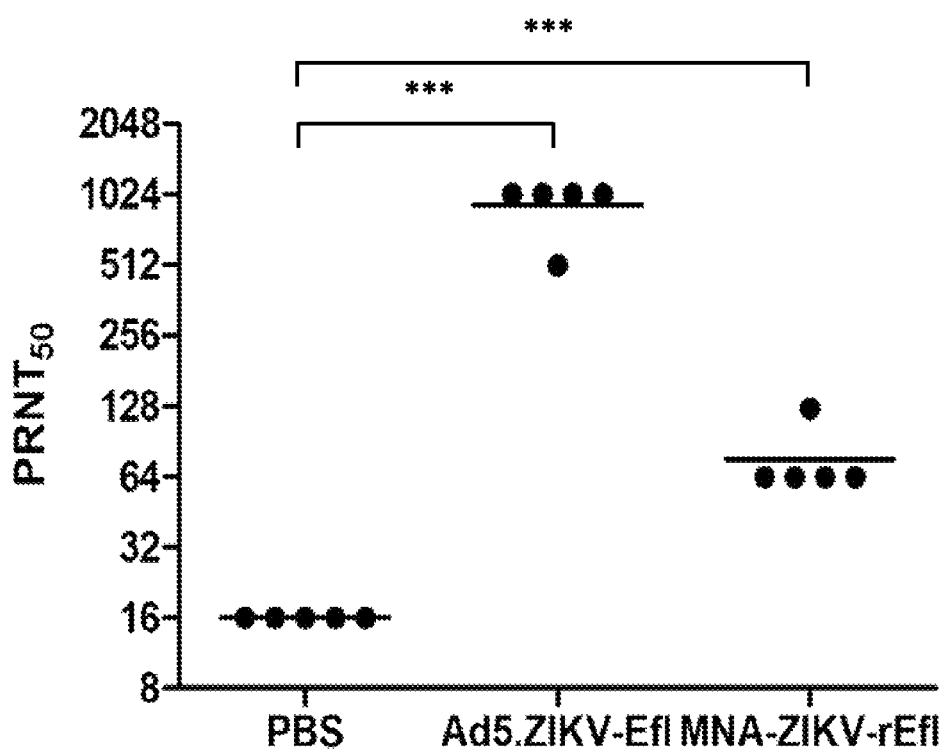

Furthermore, qualitative neutralizing activity of ZIKV antibodies was tested in a PRNT 50% assay. The presence of ZIKV-neutralizing antibodies was shown in both AdS.ZIKV-Efl and MNA-ZIKV-rEfl, although the response in the mice immunized with MNA-ZIKV-rEfl was four- to 16-fold lower than the response achieved in the mice immunized with Ad5.ZIKV-Efl. As expected, no neutralizing antibody responses were observed in the control animal group (FIG. 2c). These findings support that Ad5.ZIKV-Efl- and MNA-ZIKV-rEfl-based ZIKV E antigen vaccines are able to induce neutralizing ZIKV-specific immunity.

To further understand how the vaccine induced ZIKV E-specific immunity, neutralizing the ZIKV in vivo and protecting the animal from its pathogenic effects, a passive protection suckling mouse model was utilized. Building upon the knowledge (Dick et al., 1952, Trans R Soc Trop Med Hyg, 46, 509-20) that day 7- (but not day 14-) old suckling mice are susceptible to ZIKV infection via the i.p. route showing neurological signs, pups were obtained by mating immunized female with nonimmunized male mice at week 3 after booster immunization. Pups were challenged i.p. at seven days after birth with $10^5$ pfu of ZIKV DAKAR41542, monitored daily for mortality, and weighed for 15 days. The mean time to disease onset (10% weight loss) was slightly earlier in the pups from PBS-immunized mice than in those from MNA-ZIKV-rEfl-immunized mice, although the difference was not significant (7.75 vs. 8.25 days, P=0.1598) (Table 1).

TABLE 1

Pathogenicity of Zika virus in a mouse model

| Vaccine for dams | No. of pups | Mean time to onset of disease (days) ± SD[a] | Neurological disease (%)[b] | Neurological score[c] |
|---|---|---|---|---|
| PBS | 8 | 7.75 ± 0.88 | 100 (8/8) | 4.62 ± 1.30 |
| Ad5.ZIKV-Efl | 10 | ND | 0 (0/10)[d] | — |

TABLE 1-continued

Pathogenicity of Zika virus in a mouse model

| Vaccine for dams | No. of pups | Mean time to onset of disease (days) ± SD[a] | Neurological disease (%)[b] | Neurological score[c] |
|---|---|---|---|---|
| MNA-ZIKV-rEfl | 6 | 8.25 ± 0.50 | 83.30 (5/6)[e] | 2.80 ± 0.83* |

[a]Exhibiting >10% loss of body weight was defined as onset of disease. There were no significant differences in the average onset of disease in each group (P = 0.1598).
ND; not detected
[b]The percentage of mice showing neurological symptoms at disease onset. The number of mice showing neurological symptoms at day 10 post-infection/the number of mice showing onset of disease at day 10 post-infection
[c]Scores for the severity of neurological signs were quantified as described in Materials and Methods.
*significant difference from the score of PBS group (P < 0.05)
[d]Three out of 10 mice showed transient neurological signs (neurological score; 2.33 ± 0.57) at one time point. Significant difference from the percentage of PBS group (P < 0.0001)
[e]No significant difference from the percentage of PBS group (P = 0.2482)

Figure 3A:
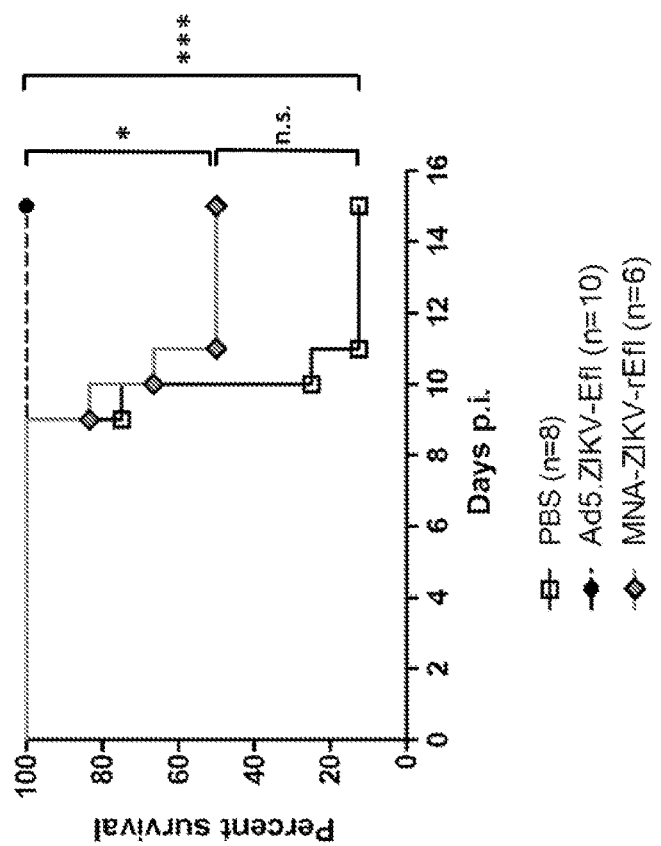
FIGS. 3A-3B. Protection from ZIKV infection in neonatal mice by maternal immunization with AdS.ZIKV-Efl and MNZ.ZIKV-rEfl. Pups were obtained by mating nonimmunized males with immunized females at five weeks after prime vaccination. Pups were challenged intraperitoneally at seven days after birth with ZIKV DAKAR41542 ($10^5$ pfu/50 µl). Body weight (FIG. 3A) and survival (FIG. 3B) were monitored for 15 days post-infection. Statistically significant differences (Tukey's test or log-rank (Mantel-Cox) test) are marked by bars and asterisks. *, $P<0.05$; , $P<0.01$; *, $P<0.001$.
Figure 3B:
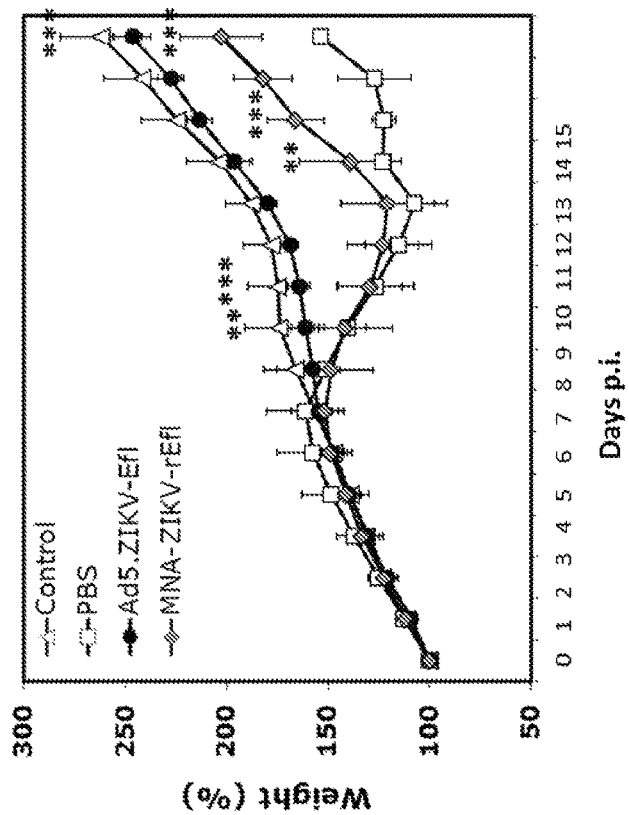
Figure 4:
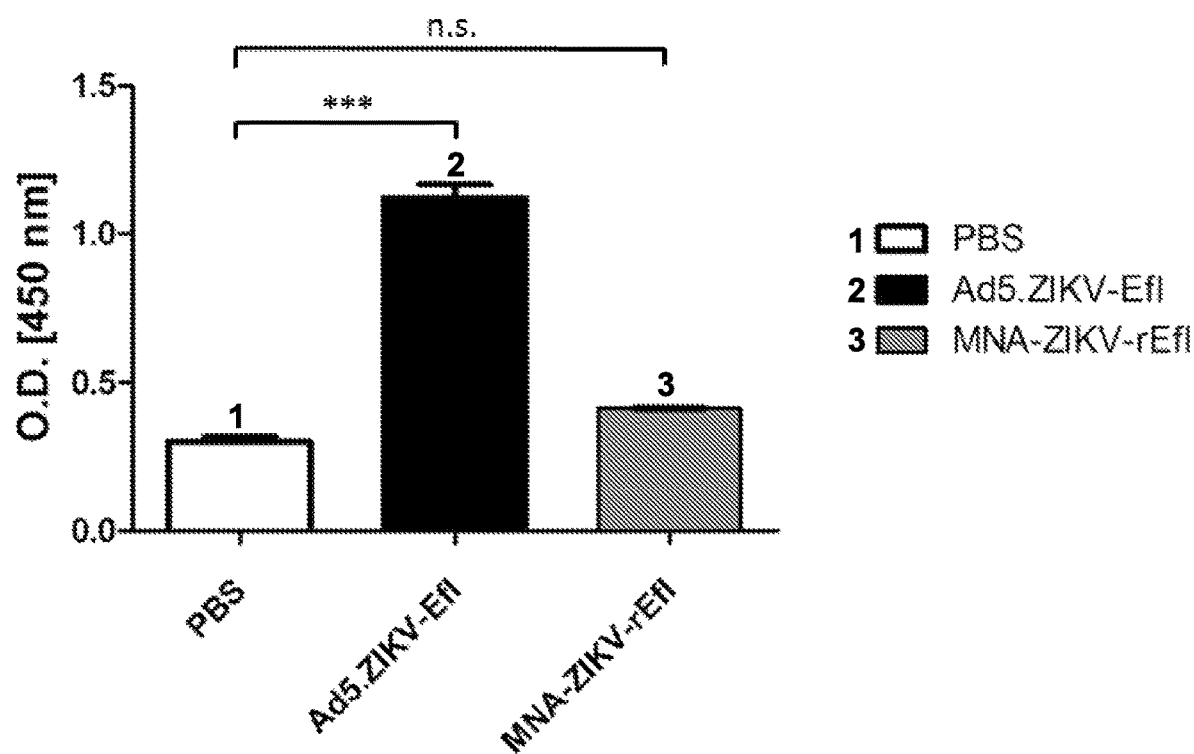
FIG. 4. Transfer of maternal ZIKV-E-specific IgG to pups. Two pups of each litter were bled at 25 days after birth to determine passive maternal antibodies and confirmed by ELISA coated with ZIKV. Statically significant differences (Tukey's test) are marked by bars and asterisks. ***, P<0.001; n.s.; statistically not significant.
Figure 5:
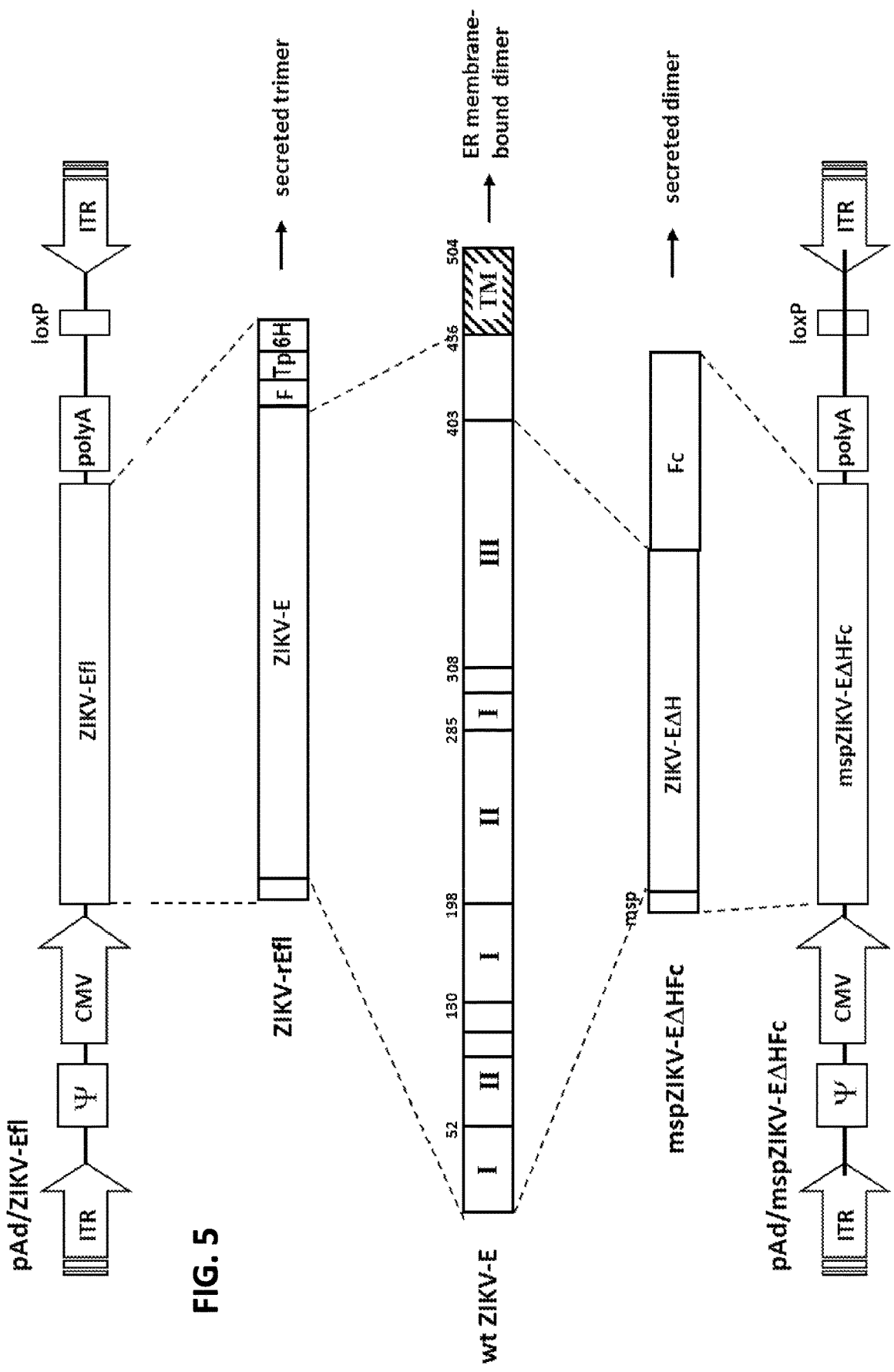
FIG. 5. Schematic diagram of additional constructs.
Figures 6A, 6B:
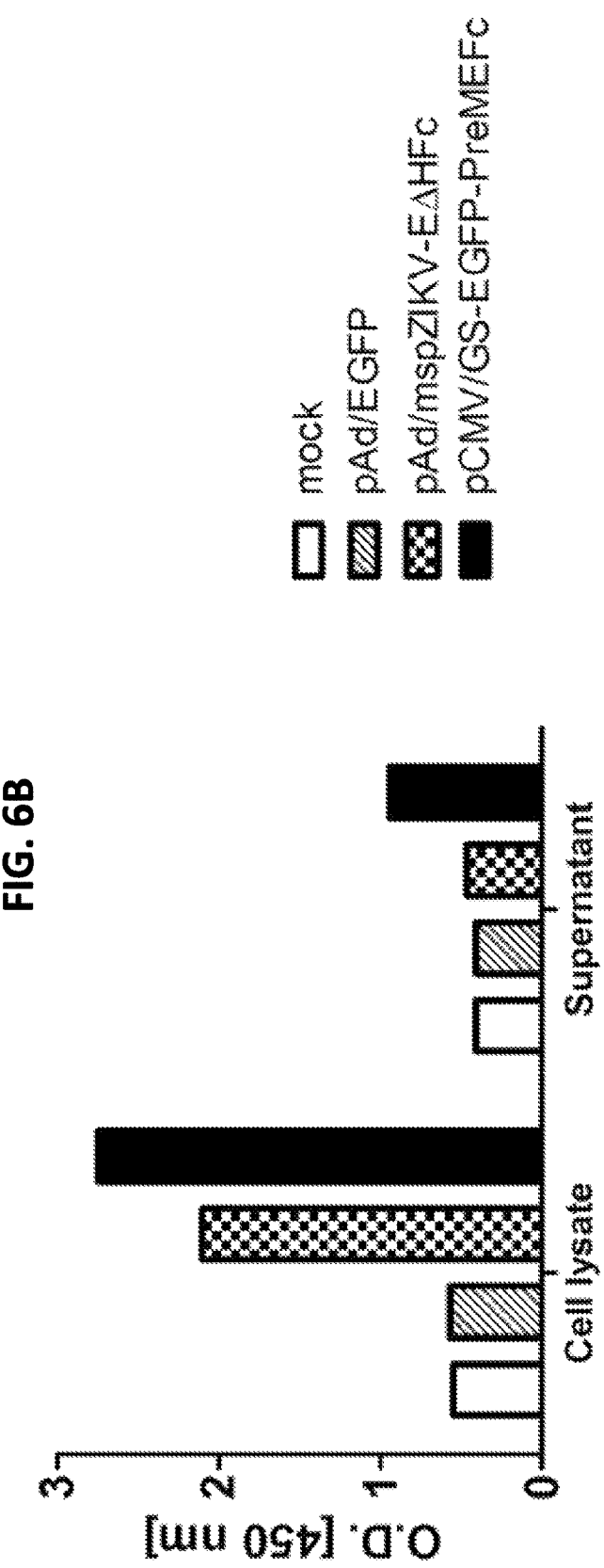
FIGS. 6A-6B. Expression of ZIKV-EFc in supernatant and cell lysate from the 293HEK cells transfected with pAd/mspZIKV-EAHFc or pCMV/GS-EGFP-PreMEFc construct.

All pups born to PBS-immunized mice showed more than a 20% body weight loss in the 10 days post-infection. However, weight loss in the MNA-ZIKV-rEfl pups was reduced and a significant difference was found from day 12 (P<0.01; P<0.001, day 13~day 15) after challenge when compared to the PBS pups. No weight loss was observed in the pups born to the dams immunized with AdS.ZIKV-Efl vaccine and no significant difference was measured between the pups of Ad5.ZIKV-Efl-immunized mice and the unchallenged control pups for the entire period. The significant difference started at day 8 (P<0.01; P<0.001, day 9~day 15) after challenge when compared to the PBS pups. (FIG. 3a). The survival rates of pups from two animals in each group were also monitored after challenge with ZIKV DAKAR41542. Survival rates of 100% (10/10) and 50% (3/6) were observed in the pups from Ad5.ZIKV-Efl- and MNA-ZIKV-rEfl-immunized dams, respectively, whereas a 12.5% (1/8) survival rate was seen in pups from PBS-immunized dams (FIG. 3b). The differences between the pups from AdS.ZIKV-Efl- and those from PBS-immunized dams and between the pups from Ads.ZIKV-Efl- and those from MNA-ZIKV-rEfl-immunized dams were statistically significant (P=0.0001 and P=0.0136, respectively). When the pups from MNA-ZIKV-rEfl- and PBS-immunized dams were compared, no significant difference in survival rate was observed (P=0.1493), indicating that the Ads.ZIKV-Efl vaccine candidates were efficient in passively protecting neonatal mice against lethal ZIKV challenge.

As expected, all pups of PBS-immunized dams showed neurological signs including loss of balance, paresis, and hindlimb paralysis, with 4.62±1.30 of neurological score. However, five out of six pups of MNA-ZIKV-rEfl-immunized dams exhibited neurological illness (no significant difference from the percentage of PBS group; P=0.2482), although the neurological severity score was significantly lower than that of pups from PBS-immunized mice (P<0.05). In contrast, the pups from AdS.ZIKV-Efl-immunized mice showed mild symptoms at one time point or no signs of neurological illness (Table 1).

Lastly, to determine the relationship between survival rate and maternally-transferred antibody, the sera from 25-day-old non-challenged pups born from immunized dams were collected and tested for reactivity with ZIKV by ELISA. The level of maternal IgG ZIKV-specific antibodies measured in pups nursed by AdS.ZIKV-Efl-immunized dams was significantly higher than that in pups nursed by PBS-immunized dams (P<0.001). However, in the pups nursed by MNA-ZIKV-Efl-immunized dams, the level of IgG antibodies against ZIKV-rEfl was not significantly higher when compared with that in pups nursed by PBS-immunized dams. These data suggest that the survival rate in pups correlated with the maternally-transferred antibody IgG titer, and although some of the animals immunized with MNA-ZIKV-rEfl were protected, the level of ZIKV-specific IgG transferred to the newborns was suboptimal.

Thus, two ZIKV vaccine candidates were constructed an analyzed. The initial evaluations indicated that the ZIKV vaccines Ads.ZIKV-Efl and MNA-ZIKV-rEfl elicited a humoral immune response in immunized C57BL/6 mice. The humoral response was characterized by high titers of antibodies to E antigen as confirmed by ELISA, as well as neutralizing titers confirmed by PRNT50 assay. Importantly, in pups born to immunized dams, ZIKV-specific immunity was passively transferred and protected them from day 7 challenge of 10 pfu of the ZIKV DAKAR41542 strain.

The Ad5.ZIKV-Efl and MNA-ZIKV-rEfl vaccines were engineered using the 2015 Brazil ZIKV strain BeH815744. The BeH815744 strain E protein differs from the DAKAR41542 strain E protein used for challenge in three amino acids (98% identity). In general, the ZIKV envelope protein is highly conserved.

Although in the presented studies the adenovirus-based Ad5.ZIKV-Efl vaccine was the most potent of the two tested ZIKV vaccine candidates, it is less likely to be used commercially. This is because the prevalence of anti-adenovirus serotype 5-neutralizing antibodies in humans limits its use as suitable clinical vaccine platform. However, the experimental use of serotype 5 adenoviral-based vaccines, as shown in this study, is an invaluable tool for the antigen vaccine selection for any given pathogen. Conversely, the MNA-delivered ZIKV vaccine MNA-ZIKV-rEfl, although not optimized for inducing neutralizing immunity in the current format, is a clinically applicable vaccine platform to target infectious diseases such as ZIKV. The geometric design of the MNA-based vaccine platform affords unique advantages for efficient delivery and targeting to the superficial skin microenvironment, which is rich in antigen-presenting cells. While immunogenicty was lower than that observed in a previously reported adjuvented and inactivated whole virus vaccine (Larocca et al., 2016, Nature), the MNA-based vaccine offers the safety and clinical advantages of a defined recombinant subunit antigen and the potential for local co-delivery of adjuvants at very low doses. Co-delivery of TLR ligand adjuvants at very low concentrations can substantially increase the immunogenicity of an influenza subunit vaccine (Weldon et al., 2012, PLoS One, 7, e41501). Importantly, the fabrication process of MNAs affords unique product advantages in reproducibility, safety, manufacturing, and distribution critical for widespread clinical deployment.

The yield of production of the ZIKV envelope E subunit protein was very low in the current format. This finding, also confirmed by a recently published ZIKV vaccine study (Larocca et al., 2016, supra), is similar to what was previously observed for other flaviviruses (Taylor et al., 2016, Virology, 496, 186-93). The low yield of E protein is probably due to the absence of preM, which is important for protein stability. For instance, expression of WNV E protein alone showed proteolytic cleavage compared to the E protein produced in the presence of preM (Taylor et al., 2016, supra). Thus, preM sequence could be included in the vaccine.

An immunocompetent mouse challenge model of ZIKV infection was utilized in the results presented herein. This approach was inspired by a 1952 publication (Dick et al., 1952, Trans R Soc Trop Med Hyg, 46, 509-20) in which ZIKV was shown to be pathogenic in newborn mice. Although this model does not recapitulate the ZIKV pathogenesis observed in humans, it is an effective model to evaluate the in vivo neutralizing activity of vaccine-induced ZIKV immunity. Other mouse models of ZIKV infection include interferon receptor-deficient mice and SJL mice (Cugola et al., 2016, Nature, 534, 267-71; Shah and Kumar, 2016, Neurotox Res, 30, 131-4; Miner et al., 2016, Cell, 165, 1081-91; Dowall et al., 2016, PLoS Negl Trop Dis, 10, e0004658; Lazear et al., 2016, Cell Host Microbe, 19, 720-30; Rossi et al., 2016, Virus. Am J Trop Med Hyg, 94, 1362-9). The SJL mice, the closest clinical model of fetal microcephaly, is also of use to evaluate the efficiency of vaccine candidates, and thus to confirm the effectiveness of the approaches disclosed herein.

Example 3

Additional Constructs

Newly assembled ZIKV immature virions have trimeric protrusions of the E. During virus maturation, ZIKV-E induces the reorganization into E homodimers. To construct the dimeric form of ZIKV-E, the trimeric domain, foldon, was replaced by the Fc of human IgG1, a human secretory signal peptide hidden Markov model (SP-HMM) was used with mouse IgG1 signal peptide (msp). The H region of ZIKV-E, which functioned in ER retention, was removed.

For the expression of dimeric ZIKV-PreMEFc from glutamine synthetase (GS) knockout CHO K1 cells in the future clinical trial, pCMV/GS-EGFP-PreMEFc was generated by subcloning the gene expressing Chinese hamster GS, EGFP, ZIKV-PreMEFc linked 2As from porcine teschovirus-1 and Equine rhinitis A virus, respectively, into the shuttle vector, pCMV-3Tag-4A (Genscript) at Hind III/Xho I sites. For detection of ZIKV-EFc protein expression, 293HEK cells were transfected with pCMV/GS-EGFP-PreMEFc, pAd/mspZIKV-EAHFc, or pAd/EGFP as a control using Lipofectamine (Invitrogen). At 48 hours post transfection, a sandwich ELISA was performed with the cell lysate and the supernatant. For these assays, a 96-well plate was coated with 1.5 μg of human IgG per well overnight at 4° C. in carbonate coating buffer (100 mM, pH 9.5) as a capture antibody and then blocked with PBS containing 0.05% Tween 20 (PBS-T) and 2% BSA for one hour. 100 μl of the supernatants and 100 μl of cell lysates diluent (1:4) were added and incubated for two hours. After the plates were washed, the detection antibody, mouse serum against ZIKV, was added to each well and incubated for two hour, followed by HRP-conjugated anti-mouse IgG (1:2000, Santacruz) for half hour. The plate was washed three times and developed with 3,3'5,5'-tetramethylbenzidine, and the reaction was stopped with 0.18M $H_2SO_4$ and absorbance at 450 nm was determined using an ELISA reader (PerkinElmer).

ELISA analysis showed expression of ZIKV-Efc protein in 293HEK cell lysate transfected with pAd/mspZIKV-EAHFc or pCMV/GS-EGFP-PreMEFc, while no expression was detected in the mock and pAd/EGFP-transfected cell. However, ZIKV-Efc was observed only in the supernatant of 293HEK cell transfected with pCMV/GS-EGFP-PreMEFc. This finding is similar to what was previously observed for other flaviviruses (Taylor et al., 2016, Virology, 496, 186-93). The low yield of E protein from pAd/mspZIKV-EAHFc is probably due to the absence of preM, which is important for protein stability. Thus, the inclusion of preM sequence may be important in ZIKV E-based vaccine development.

Example 4

Microneedle Arrays, Adjuvants and Additional Studies

A skin-targeting vaccine delivery technology was designed specifically to afford advantages in immunogenicity, economy, and safety that will enable broad clinical deployment. The dissolvable microneedle arrays (MNAs) enable efficient, precise, and reproducible delivery of biologically-active vaccines to the skin. Further, this MNA delivery platform is directly applicable to patient-friendly, clinical vaccination. Because the microneedles in these arrays have been engineered to not penetrate to the depth of vascular or neural structures, delivery to human skin is both painless and bloodless. The fabrication process is flexible and enables simple and rapid low cost production with efficient scale-up potential. These structural and manufacturing advantages, coupled with a final product that is stable at room temperature and inexpensive to transport and store, makes this technology enabling broad and rapid clinical vaccine deployment applicable to the prevention and/or treatment of a broad range of human diseases.

Adjuvants are used to increase the immunogenicity of the subunit Zika vaccines. As discussed above, when the E antigen was delivered by adenoviral vector, the potency of the vaccine was higher than the correspondent MNA delivered vaccine. This in part is due to the inherent adjuvant activity of adenoviral vaccine platform. One of the reason adenoviral vector is such good vaccine platform is because its ability to induce STING pathway activation. Thus, cyclic dinucleotides (CDNs) can be used as Zika vaccine adjuvants. 2'3'-cGAMP (cyclic [G(2',5')pA(3',5')p]) is a CDN produced in mammalian cells by cGAS (cGAMP synthase) in response to double-stranded DNA in the cytoplasm. 2'3'-cGAMP is also referred to as "noncanonical" cGAMP due to the presence of the atypical 2'-5' phosphodiester linkage between the guanosine and the adenosine. Structural and functional studies revealed that noncanonical 2'3'-cGAMP is distinct from the canonical 3'3'-cGAMP produced by bacteria (Diner et al., Cell Rep. 2013; 3(5):1355-61; Gao et al., Cell. 2013; 153(5):1094-107). CDNs are a relatively new class of adjuvants that have been shown to increase vaccine potency (Dubensky et al., Ther Adv Vaccines. 2013; 1(4):131-43). CDNs activate innate immunity by directly binding the endoplasmic reticulum-resident receptor STING (stimulator of interferon genes), activating a signaling pathway that induces the expression of interferon-β (IFN-β) and also nuclear factor-κB (NF-κB) dependent inflammatory cytokines. Recently, it has been reported that 2'3'-cGAMP is an effective adjuvant that boosts the production of antigen-specific antibodies and T cell responses in mice (Li et al., Science. 2013; 341(6152): 1390-4). Thus, in the context of ZIKV-MNA-delivered subunit vaccines, the adjuvant efficacy of the 2'3'-cGAMP and 3'3'-cAMP can be used, and their activity can be compared to the poly(I:C) adjuvant.

Highly reproducible biocompatible dissolvable CMC-based MNAs were developed that effectively penetrate and deliver integrated cargo to mouse and human skin. The cargo is taken up by APCs and transported to the draining lymph node, where transgenic antigen associated with APC populations can be defined. Briefly, fabrication of MNAs, integration of several protein and small molecule cargos, and efficient delivery to both mouse and human skin has been documented. This novel delivery system integrates cargo into dissolvable CMC microneedles. Each MNA is composed of a 10×10 array of microneedles covering a 6×6 mm area (FIG. 7A). Each individual needle is 700 μm high with a 300 apex angle and a 200 μm base (FIG. 7B). Several features of the design, including the obelisk geometry and filet angles (FIG. 7B), have been designed to optimize skin penetration and delivery efficiency. When MNA are applied to the skin, the microneedles rapidly dissolve (~5 min), depositing the cargo in the localized area of skin penetration (FIG. 7C). To evaluate penetration capability, MNAs were initially tested for piercing on water-based model elastic substrates and on full thickness human skin (FIG. 8A-8C). The model elastic substrate consisted of 10% CMC and 10% porcine gelatin in phosphate buffered saline (PBS) gelled at 4° C. for 24 hours or longer. The surface of the elastics was covered with 100 μm thick Parafilm to prevent the immediate contact of the needle-tips and the patch materials with the water based model elastics. To enhance stereo microscopic-imaging, trypan blue tracer dye (Sigma Chem., cat # T6146) was incorporated into the tip section of the microneedles at 0.1% concentration (FIG. 8A). The patches were applied to the targets using a specifically designed spring-loaded applicator and analyzed after 15 min. exposure to the skin. Based on gross observation, the microneedles penetrated and released a substantial amount of tracer dye into the full thickness human skin (FIG. 8B, 8C), and mouse skin. Images of recovered patches revealed considerable degradation of the needles (FIG. 8A), indicating the dissolution of the CMC matrix. To evaluate cutaneous delivery of particulate antigen in vivo, fluorescent particle-containing MNAs were applied to the dorsal aspect of the ears of anesthetized mice. After five minutes, the patches were removed and the mice resumed their normal activity. Two days later, mice were sacrificed and ear skin and draining lymph nodes were analyzed for the presence of fluorescent particles. Consistent with observations of human skin, particulates were evident in the skin excised from the array application site (FIG. 8D). Further, at the two day time point, a substantial numbers of particles were evident in the draining lymph node cells in close association with APCs, including macrophages (FIG. 8E) and DCs (FIG. 8F). The skin is rich in readily-accessible DCs and has long been regarded as a highly immunogenic target for vaccine delivery (Larregina et al., J Invest Dermatol. 2005; 124(1):1-12).

Figure 9A:
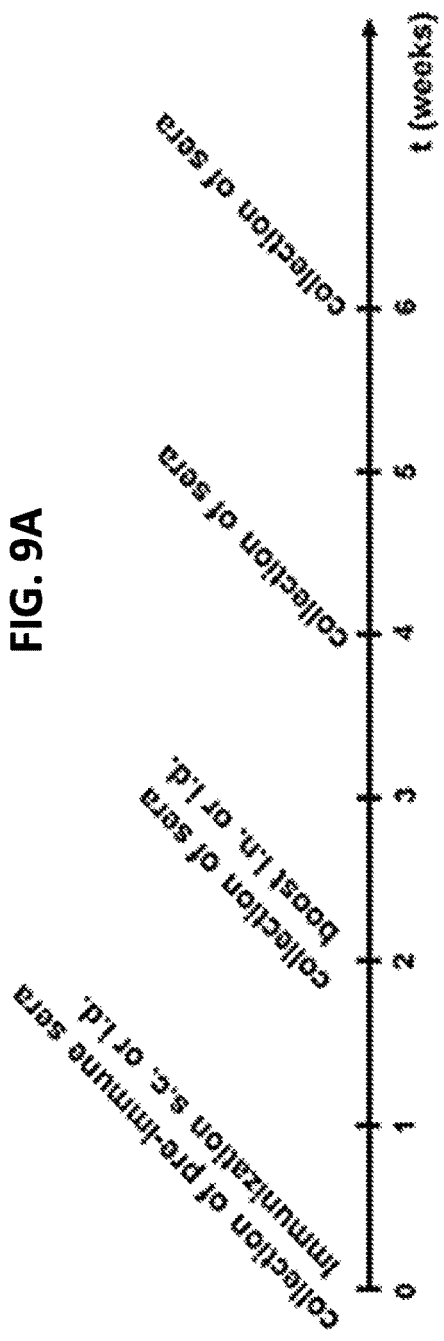
Figure 9B:
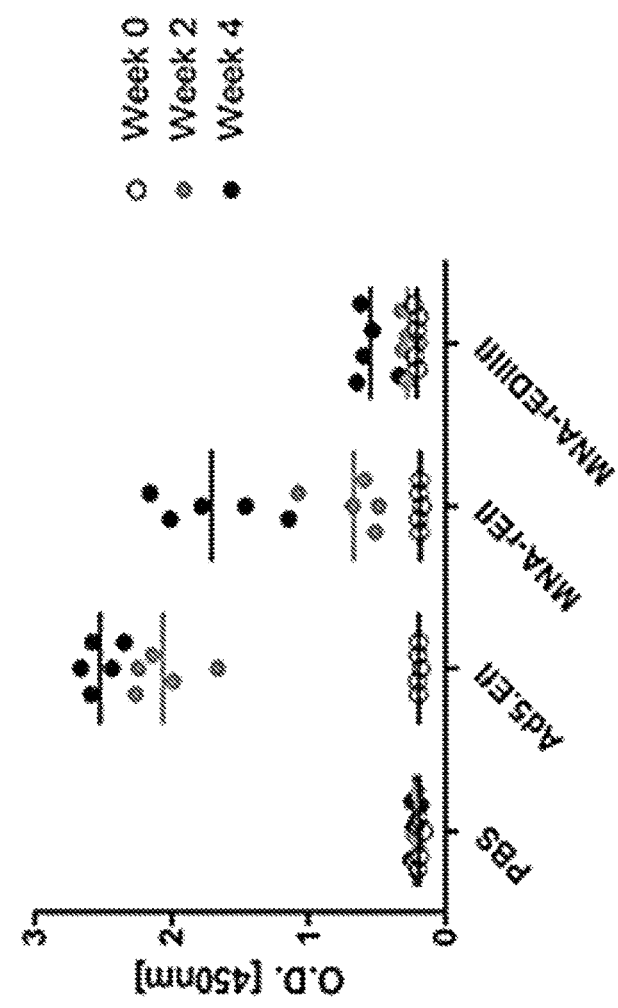
Figure 9C:
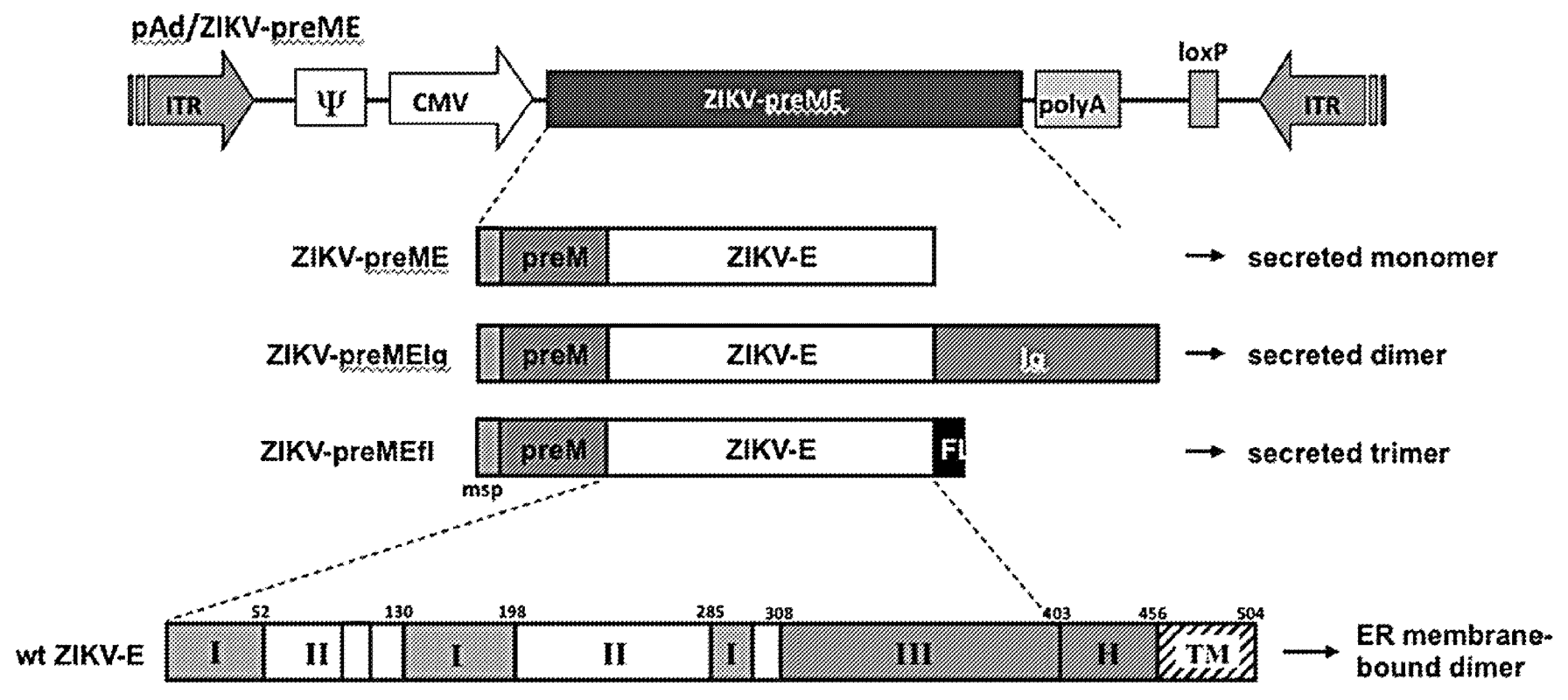

As disclosed above, ZIKV subunit vaccines expression systems were produced based on E1/E3-deleted recombinant adenovirus (Ad5) encoding for a signal peptide, the codon-optimized ectodomain of the ZIKV envelope gene (ZIKV-E) alone or fused to the hinge and Fc region of human IgG1 (ZIKV-EhIg) or T4 fibritin foldon domain (ZIKV-Efl) (FIG. 9). This led to expression of secreted monomeric, dimeric, or trimeric, envelope ectodomains. The monomeric and trimeric subunit antigens were designed with a polyhistidine-tag and a Tobacco Etch Virus (TEV) protease cleavage sequence to facilitate downstream large-scale purification compatible with manufacturing. The Zika-E (GENBANK® KU365780.1, as available Dec. 30, 2016, incorporated by reference herein) gene was codon-optimized for optimal expression in mammalian cells by the UpGene codon optimization algorithm and synthesized as previously described (Gao et al., Biotechnol Prog. 2004 March-April; 20(2):443-8).

For the expression of dimer or tirmer, codon optimized hIg or foldon domain gene was inserted in the C terminal of ZIKV-E. Subsequently, replication-defective adenovirus 5, designated as Ad.ZIKV-E, Ad5.ZIKV-EhIg, Ad.ZIKV-Efl, were generated by loxP homologous recombination. The purified six recombinant proteins named ZIKV-rE, ZIKV-rEhIg, ZIKV-rEfl, were generated from the supernatant of 293 infected cells using His60 Ni Superflow Resin (Clontech) under native conditions and are used as a subunit vaccines.

Figure 10:
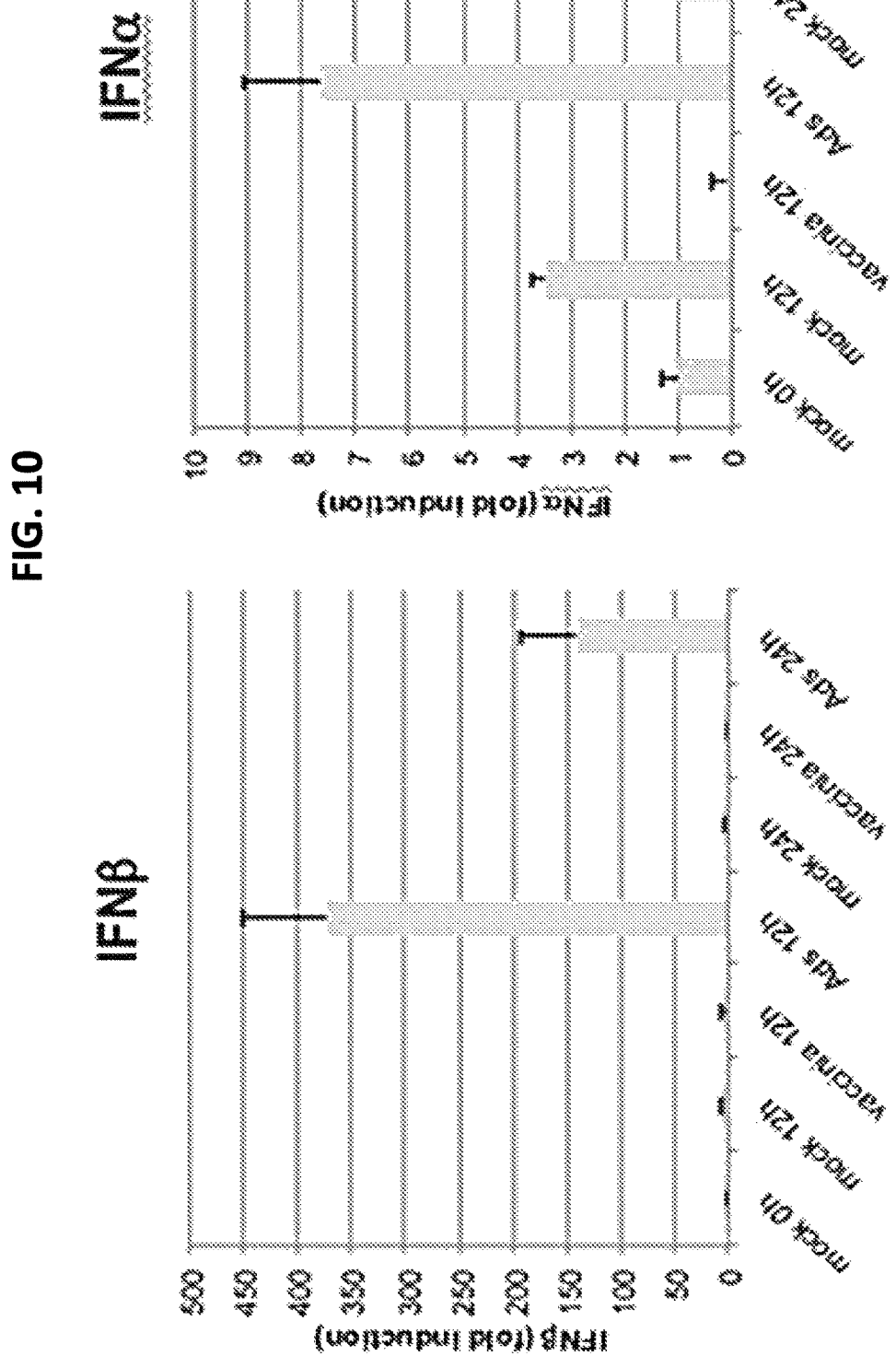
FIG. 10. Activation of STING pathway in mouse bone marrow derived dendritic cells infected with adenovirus. Activation measured as induction of interferon α or interferon 3.

In additional experiments, the in vitro induction of STING pathway by adenoviral vectors was investigated by infecting day 7 bone marrow derived GM/IL4 murine dendritic cells (mDCs). A 12-well plate was seeded 7×10e5 mDCs per well and 20 MOI of adenovirus or 10 MOI of vaccinia virus was infected. As surrogate marker for STING pathway activation, the induction of IFNα and IFNβ was measured at 12 and 24 hours post infection using real-time PCR. As shown in FIG. 10 adenoviral infection induced both IFNα and IFNβ. This data is in support of use of adjuvants, such as the cyclic di-nucleotide (STING pathway simulators). Vaccine strategies are shown in the Tables 2 and 3 below:

TABLE 2

|  | Group 1 | Group 2 | Group 3 | Group 4 |
| --- | --- | --- | --- | --- |
| Day 0 PRIME | MNA.empty | MNA ZIKV-preME | MNA ZIKV-preMEIg | MNA ZIKV-preMEfl |
| Day 14 BOOST | MNA.empty | MNA ZIKV-preME | MNA ZIKV-preMEIg | MNA ZIKV-preMEfl |

TABLE 3

|  | Group 1 | Group 2 | Group 3 | Group 4 | Group 5 |
| --- | --- | --- | --- | --- | --- |
| Day 0 PRIME | MNA.empty | MNA.ZIKV-selected | MNA.ZIKV-selected + poly(I:C) | MNA.ZIKV-selected + 3'2' cGAMP VacciGrade | MNA.ZIKV-selected + 3'3' cAMP VacciGrade |
| Day 14 BOOST | MNA.empty | MNA.ZIKV-selected | MNA.ZIKV-selected + poly(I:C) | MNA.ZIKV-selected + 3'2' cGAMP VacciGrade | MNA.ZIKV-selected + 3'3' cAMP VacciGrade |

In order to establish a ZIKV challenge mouse model, 7-day-old C57BL/6 suckling complete paralysis and no spontaneous movement; and 3, inability of movement. Scoring for loss of balance was assigned as follows: 0, normal; 1, leaning of head or trunk posture to one side; and 2, inability to retain posture and falling to one side or a circling movement to one side. Neurological disease was defined as a total score of >1.0. 10e6, 10e5, and 10e4 pfu of ZIKV-infected mice showed clear signs of neurological disease on 7, 8, and 10 days postinfection, respectively. Neurological disease progressed fast and coincided with a pronounced loss of body weight because their inability to feed.

Additional vaccination strategies are shown below:

TABLE 4

| | Group 1 | Group 2 |
|---|---|---|
| Day 0 PRIME | MNA.Empty | MNA.ZIKV-selected +/− adjuvant selected |
| Day 14 BOOST | MNA.Empty | MNA.ZIKV-selected +/− adjuvant selected |
| | 5 mice | 5 mice |
| Day 70-80 | Suckling mice ZIKV | Suckling mice ZIKV |

TABLE 4-continued

| Group 1 | Group 2 |
|---|---|
| DAKAR41542 Challenge | DAKAR41542 Challenge |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An immunogen comprising a fusion protein, wherein the fusion protein comprises a Zika virus (ZIKV) envelope protein, a signal peptide, and a multimerization domain, wherein:
   the signal peptide is a human secretory signal peptide hidden Markov model, wherein the human secretory signal peptide hidden Markov model comprises an amino acid sequence at least 95% identical to SEQ ID NO: 2; and
   the multimerization domain is an immunoglobulin Fc domain, a T4 fibritin foldon trimerization domain, or a human collagen XV trimerization domain.

2. The immunogen of claim 1, wherein the human secretory signal peptide hidden Markov model comprises the amino acid sequence of SEQ ID NO: 2.

3. An immunogen comprising a fusion protein, wherein the fusion protein comprises a Zika virus (ZIKV) envelope protein, a signal peptide, and a multimerization domain, wherein:
   the signal peptide is an IgG signal peptide, wherein:
   a) the IgG signal peptide is a mouse IgG signal peptide comprising an amino acid sequence at least 95% identical to SEQ ID NO: 3; or
   b) the IgG signal peptide is a human IgG signal peptide comprising an amino acid sequence at least 95% identical to SEQ ID NO: 4,
   and wherein
   c) the multimerization domain is an immunoglobulin Fc domain, a T4 fibritin foldon trimerization domain, or a human collagen XV trimerization domain.

4. The immunogen of claim 3, wherein the mouse IgG signal peptide comprises the amino acid sequence of SEQ ID NO: 3.

5. The immunogen of claim 3, wherein the human IgG signal peptide comprises the amino acid sequence of SEQ ID NO: 4.

6. An immunogen comprising a fusion protein, wherein the fusion protein comprises a Zika virus (ZIKV) envelope protein, a signal peptide, and a multimerization domain, wherein:
   the signal peptide is a prM signal peptide, wherein the prM signal peptide is a human IgG signal peptide comprising an amino acid sequence at least 95% identical to SEQ ID NO: 5 and the multimerization domain is an immunoglobulin Fc domain, a T4 fibritin foldon trimerization domain, or a human collagen XV trimerization domain.

7. The immunogen of claim 6, wherein the prM signal peptide comprises the amino acid sequence of SEQ ID NO: 5.

8. An immunogen comprising a fusion protein, wherein the fusion protein comprises a Zika virus (ZIKV) envelope protein, a signal peptide, and a multimerization domain, wherein:
   the signal peptide is a premembrane (prM) signal peptide, an IgG signal peptide, or a human secretory signal peptide hidden Markov model, and
   wherein the multimerization domain is an immunoglobulin Fc domain, and wherein the immunoglobulin Fc domain comprises an amino acid sequence at least 95% identical to the amino acid sequence of SEQ ID NO: 9, and wherein the immunoglobulin Fc domain forms a dimer in vivo.

9. The immunogen of claim 8, wherein the immunoglobulin Fc domain comprises the amino acid sequence of SEQ ID NO: 9.

10. An immunogen comprising a fusion protein, wherein the fusion protein comprises a Zika virus (ZIKV) envelope protein, a signal peptide, and a multimerization domain, wherein:
    the signal peptide is a premembrane (prM) signal peptide, an IgG signal peptide, or a human secretory signal peptide hidden Markov model, and
    wherein the multimerization domain is a T4 fibritin foldon trimerization domain, and wherein the T4 fibritin foldon trimerization domain comprises an amino acid sequence at least 95% identical to the amino acid sequence of SEQ ID NO: 10, wherein the fibritin foldon trimerization domain forms a trimer in vivo.

11. The immunogen of claim 10, wherein the T4 fibritin foldon trimerization domain comprises the amino acid sequence of SEQ ID NO: 10.

12. An immunogen comprising a fusion protein, wherein the fusion protein comprises a Zika virus (ZIKV) envelope protein, a signal peptide, and a multimerization domain, wherein:
    the signal peptide is a premembrane (prM) signal peptide, an IgG signal peptide, or a human secretory signal peptide hidden Markov model, and
    wherein the multimerization domain is the a human collagen XV trimerization domain, and wherein the human collagen XV trimerization domain comprises an amino acid sequence at least 95% identical to the amino acid sequence of SEQ ID NO: 11, wherein the human collagen XV trimerization domain forms a trimer in vivo.

13. The immunogen of claim 12, wherein the human collagen XV trimerization domain comprises the amino acid sequence of SEQ ID NO: 11.

14. An immunogen comprising a fusion protein, wherein the fusion protein comprises a Zika virus (ZIKV) envelope protein, a signal peptide, a multimerization domain, and a premembrane (prM) of ZIKV wherein:
    the signal peptide is a prM signal peptide, an IgG signal peptide, or a human secretory signal peptide hidden Markov model, and
    the multimerization domain is an immunoglobulin Fc domain, a T4 fibritin foldon trimerization domain, or a human collagen XV trimerization domain and the prM of ZIKV comprises an amino acid sequence at least 95% identical to SEQ ID NO: 8.

15. The immunogen of claim 14, wherein the prM of ZIKV comprises the amino acid sequence of SEQ ID NO: 8.

16. A dissolvable microneedle array for transdermal insertion into a subject for promoting an immune response against Zika virus (ZIKV) in a subject in need thereof, the array comprising:

a base portion; and a plurality of microneedles extending from the base portion and containing an immunogen, and optionally at least one adjuvant, wherein the immunogen comprises a fusion protein, wherein the fusion protein comprises a Zika virus (ZIKV) envelope protein, a signal peptide, and a multimerization domain, wherein:

the signal peptide is a premembrane (prM) signal peptide, an IgG signal peptide, or a human secretory signal peptide hidden Markov model, and the multimerization domain is an immunoglobulin Fc domain, a T4 fibritin foldon trimerization domain, or a human collagen XV trimerization domain.

17. The dissolvable microneedle array of claim 16, wherein the each microneedle in the plurality of microneedles are pre-formed to have a shape that comprises a first cross-sectional dimension at a top portion, a second cross-sectional dimension at a bottom portion, and a third cross-sectional dimension at an intermediate portion, wherein the intermediate portion is located between the top portion and the bottom portion, and the third cross-sectional dimension is greater than the first and second cross-sectional dimensions.

18. The dissolvable microneedle array of claim 16, wherein each microneedle in the plurality of microneedles comprises a plurality of layers of dissoluble biocompatible material.

19. The dissolvable microneedle array of claim 18, wherein the dissoluble biocompatible material is carboxymethylcellulose.

20. A method of eliciting an immune response against Zika virus (ZIKV) in a subject, comprising contacting the skin of the subject with the microneedle array of claim 16, thereby delivering the immunogen to the skin of the subject and eliciting the immune response against ZIKV.

21. The method of claim 20, wherein the subject is a human.

22. The method of claim 21, wherein the subject is a female.

23. The method of claim 22, wherein the female is of an age wherein she can bear children.

24. The method of claim 23, wherein the female is pregnant.

25. The dissolvable microneedle array for transdermal insertion of claim 16, wherein the signal peptide is the human secretory signal peptide hidden Markov model, and wherein the human secretory signal peptide hidden Markov model comprises an amino acid sequence at least 95% identical to SEQ ID NO: 2.

26. The dissolvable microneedle array for transdermal insertion of claim 16, wherein the signal peptide is the IgG signal peptide, and wherein:

a) the IgG signal peptide is a mouse IgG signal peptide comprising an amino acid sequence at least 95% identical to SEQ ID NO: 3; or b) the IgG signal peptide is a human IgG signal peptide comprising an amino acid sequence at least 95% identical to SEQ ID NO: 4.

27. The dissolvable microneedle array for transdermal insertion of claim 16, wherein the signal peptide is the prM signal peptide, and wherein the prM signal peptide comprises an amino acid sequence at least 95% identical to SEQ ID NO: 5.

28. The dissolvable microneedle array for transdermal insertion of claim 16, wherein the multimerization domain is the immunoglobulin Fc domain, and wherein the immunoglobulin Fc domain comprises an amino acid sequence at least 95% identical to the amino acid sequence of SEQ ID NO: 9, and wherein the immunoglobulin Fc domain forms a dimer in vivo.

29. The dissolvable microneedle array for transdermal insertion of claim 16, wherein the multimerization domain is the human collagen XV trimerization domain, and wherein the human collagen XV trimerization domain comprises an amino acid sequence at least 95% identical to the amino acid sequence of SEQ ID NO: 11, wherein the human collagen XV trimerization domain forms a trimer in vivo.

30. The dissolvable microneedle array for transdermal insertion of claim 16, wherein prM comprises an amino acid sequence at least 95% identical to SEQ ID NO: 8.

31. A nucleic acid molecule encoding the immunogen of claim 1.

32. A vector comprising the nucleic acid molecule of claim 31.

33. The vector of claim 32, wherein the vector is an adenoviral vector.

34. An immunogenic composition comprising the immunogen of claim 1, or a vector encoding the immunogen, and a pharmaceutically acceptable carrier.

35. The immunogenic composition of claim 34, further comprising one or more adjuvants.

36. A nucleic acid molecule encoding the immunogen of claim 3.

37. A vector comprising the nucleic acid molecule of claim 36.

38. The vector of claim 37, wherein the vector is an adenoviral vector.

39. An immunogenic composition comprising the immunogen of claim 3, or a vector encoding the immunogen, and a pharmaceutically acceptable carrier.

40. The immunogenic composition of claim 39, further comprising one or more adjuvants.

41. A nucleic acid molecule encoding the immunogen of claim 6.

42. A vector comprising the nucleic acid molecule of claim 41.

43. The vector of claim 42, wherein the vector is an adenoviral vector.

44. An immunogenic composition comprising the immunogen of claim 6, or a vector encoding the immunogen, and a pharmaceutically acceptable carrier.

45. The immunogenic composition of claim 44, further comprising one or more adjuvants.

46. A nucleic acid molecule encoding the immunogen of claim 10.

47. A vector comprising the nucleic acid molecule of claim 46.

48. The vector of claim 47, wherein the vector is an adenoviral vector.

49. An immunogenic composition comprising the immunogen of claim 10, or a vector encoding the immunogen, and a pharmaceutically acceptable carrier.

50. The immunogenic composition of claim 49, further comprising one or more adjuvants.

51. A nucleic acid molecule encoding the immunogen of claim 12.

52. A vector comprising the nucleic acid molecule of claim 51.

53. The vector of claim 52, wherein the vector is an adenoviral vector.

54. An immunogenic composition comprising the immunogen of claim 12, or a vector encoding the immunogen, and a pharmaceutically acceptable carrier.

55. The immunogenic composition of claim 54, further comprising one or more adjuvants.

56. A nucleic acid molecule encoding the immunogen of claim 14.

57. A vector comprising the nucleic acid molecule of claim 56.

58. The vector of claim 57, wherein the vector is an adenoviral vector.

59. An immunogenic composition comprising the immunogen of claim 14, or a vector encoding the immunogen, and a pharmaceutically acceptable carrier.

60. The immunogenic composition of claim 59, further comprising one or more adjuvants.

61. The immunogen of claim 1, wherein the ZIKV envelope protein comprises an amino acid sequence at least 95% identical to SEQ ID NO: 6 or SEQ ID NO: 7.

62. The immunogen of claim 61, wherein the ZIKV envelope protein comprises the amino acid sequence of SEQ ID NO: 6 or SEQ ID NO: 7.

63. The immunogen of claim 3, wherein the ZIKV envelope protein comprises an amino acid sequence at least 95% identical to SEQ ID NO: 6 or SEQ ID NO: 7.

64. The immunogen of claim 63, wherein the ZIKV envelope protein comprises the amino acid sequence of SEQ ID NO: 6 or SEQ ID NO: 7.

65. The immunogen of claim 6, wherein the ZIKV envelope protein comprises an amino acid sequence at least 95% identical to SEQ ID NO: 6 or SEQ ID NO: 7.

66. The immunogen of claim 65, wherein the ZIKV envelope protein comprises the amino acid sequence of SEQ ID NO: 6 or SEQ ID NO: 7.

67. The immunogen of claim 10, wherein the ZIKV envelope protein comprises an amino acid sequence at least 95% identical to SEQ ID NO: 6 or SEQ ID NO: 7.

68. The immunogen of claim 67, wherein the ZIKV envelope protein comprises the amino acid sequence of SEQ ID NO: 6 or SEQ ID NO: 7.

69. The immunogen of claim 12, wherein the ZIKV envelope protein comprises an amino acid sequence at least 95% identical to SEQ ID NO: 6 or SEQ ID NO: 7.

70. The immunogen of claim 69, wherein the ZIKV envelope protein comprises the amino acid sequence of SEQ ID NO: 6 or SEQ ID NO: 7.

71. The immunogen of claim 14, wherein the ZIKV envelope protein comprises an amino acid sequence at least 95% identical to SEQ ID NO: 6 or SEQ ID NO: 7.

72. The immunogen of claim 71, wherein the ZIKV envelope protein comprises the amino acid sequence of SEQ ID NO: 6 or SEQ ID NO: 7.

* * * * *

UNITED STATES PATENT AND TRADEMARK OFFICE
CERTIFICATE OF CORRECTION

PATENT NO. : 10,913,776 B2  
APPLICATION NO. : 16/337363  
DATED : February 9, 2021  
INVENTOR(S) : Gambotto et al.

Page 1 of 1

It is certified that error appears in the above-identified patent and that said Letters Patent is hereby corrected as shown below:

In the Specification

Column 1, beginning at Line 13, please insert:  
--STATEMENT OF GOVERNMENT SUPPORT  
This invention was made with government support under Grant No. AI130180 awarded by the National Institutes of Health (NIH). The government has certain rights in the invention.--

Signed and Sealed this  
Sixth Day of April, 2021

Drew Hirshfeld  
*Performing the Functions and Duties of the  
Under Secretary of Commerce for Intellectual Property and  
Director of the United States Patent and Trademark Office*